(12) United States Patent
Tyler

(10) Patent No.: US 10,213,600 B2
(45) Date of Patent: Feb. 26, 2019

(54) HYBRID METHOD FOR MODULATING UPPER AIRWAY FUNCTION IN A SUBJECT

(71) Applicant: CASE WESTERN RESERVE UNIVERSITY, Cleveland, OH (US)

(72) Inventor: Dustin J. Tyler, Highland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 210 days.

(21) Appl. No.: 15/296,070

(22) Filed: Oct. 18, 2016

(65) Prior Publication Data

US 2017/0036018 A1    Feb. 9, 2017

Related U.S. Application Data

(60) Division of application No. 14/607,448, filed on Jan. 28, 2015, now Pat. No. 9,517,340, which is a continuation of application No. 12/949,562, filed on Nov. 18, 2010, now Pat. No. 8,983,610.

(60) Provisional application No. 61/262,347, filed on Nov. 18, 2009.

(51) Int. Cl.
   *A61N 1/36*   (2006.01)
   *A61N 1/05*   (2006.01)

(52) U.S. Cl.
   CPC .......... *A61N 1/3601* (2013.01); *A61N 1/0551* (2013.01); *A61N 1/0519* (2013.01); *A61N 1/0548* (2013.01)

(58) Field of Classification Search
   CPC ...... A61N 1/0519; A61N 1/0548; A61N 1/36; A61N 1/3601

USPC .................................................... 607/42, 48
See application file for complete search history.

(56) References Cited

U.S. PATENT DOCUMENTS

| | | | |
|---|---|---|---|
| 4,907,602 A | 3/1990 | Sanders | |
| 5,016,647 A | 5/1991 | Sanders | |
| 5,725,564 A | 3/1998 | Freed et al. | |
| 5,987,359 A | 11/1999 | Freed et al. | |
| 6,174,278 B1* | 1/2001 | Jaeger .................. | A61B 5/0031 600/23 |
| 7,280,873 B2 | 10/2007 | Freed et al. | |
| 7,606,623 B2 | 10/2009 | Ludlow et al. | |
| 7,672,728 B2 | 3/2010 | Libbus et al. | |
| 7,797,050 B2* | 9/2010 | Libbus .................. | A61N 1/3611 607/42 |
| 7,805,195 B2 | 9/2010 | Zealear | |
| 7,890,178 B2* | 2/2011 | Testerman ......... | A61N 1/36085 607/48 |
| 8,983,610 B2 | 3/2015 | Tyler | |
| 2002/0010495 A1 | 1/2002 | Freed et al. | |
| 2003/0093128 A1 | 5/2003 | Freed et al. | |
| 2007/0150006 A1* | 6/2007 | Libbus ............... | A61N 1/36185 607/2 |
| 2007/0293926 A1 | 12/2007 | Dunlay et al. | |
| 2008/0071244 A1* | 3/2008 | Lindenthaler ...... | A61B 17/3468 604/500 |

(Continued)

*Primary Examiner* — Christopher A Flory
(74) *Attorney, Agent, or Firm* — Tarolli, Sundheim, Covell & Tummino LLP

(57) ABSTRACT

A hybrid method is provided for modulating upper airway function in a subject. The method includes applying first and second therapy signals to the subject to modulate at least one extrinsic laryngeal muscle and at least one intrinsic laryngeal muscle to synergistically control laryngeal motion and vocal fold movement, respectively.

13 Claims, 24 Drawing Sheets

(56) References Cited

U.S. PATENT DOCUMENTS

| | | | |
|---|---|---|---|
| 2008/0071245 A1 | 3/2008 | Muller et al. | |
| 2008/0771244 | 3/2008 | Lindenthaler | |
| 2008/0208280 A1* | 8/2008 | Lindenthaler | A61B 5/4836 |
| | | | 607/42 |
| 2008/0306373 A1 | 12/2008 | Kandori et al. | |
| 2009/0054980 A1 | 2/2009 | Ludlow et al. | |
| 2009/0177127 A1* | 7/2009 | Sherman | A61H 31/00 |
| | | | 601/41 |
| 2009/0187124 A1 | 7/2009 | Ludlow et al. | |
| 2010/0049103 A1 | 2/2010 | Ludlow et al. | |
| 2010/0121406 A1* | 5/2010 | Libbus | A61N 1/36185 |
| | | | 607/42 |
| 2010/0312302 A1* | 12/2010 | Zealear | A61B 5/087 |
| | | | 607/42 |
| 2012/0150255 A1* | 6/2012 | Lindenthaler | A61N 1/0553 |
| | | | 607/42 |
| 2013/0245486 A1* | 9/2013 | Simon | A61N 1/36021 |
| | | | 600/546 |
| 2014/0200623 A1* | 7/2014 | Lindenthaler | A61N 1/0553 |
| | | | 607/42 |

* cited by examiner

HYBRID METHOD FOR MODULATING UPPER AIRWAY FUNCTION IN A SUBJECT

RELATED APPLICATION

This application is a divisional of U.S. patent application Ser. No. 14/607,448, filed Jan. 28, 2015, entitled "Hybrid Method for Modulating Upper Airway Function in a Subject", which is a continuation of U.S. patent application Ser. No. 12/949,562, filed Nov. 18, 2010, entitled "Hybrid Method for Modulating Upper Airway Function in a Subject" (now U.S. Pat. No. 8,983,610), which claims priority from U.S. Provisional Application No, 61/262,347, filed Nov. 18, 2009 (now Expired). The entirety of these applications are hereby incorporated by reference.

TECHNICAL FIELD

The present invention relates generally to a hybrid method for modulating upper airway function in a subject, and more particularly to a hybrid method for treating laryngeal disorders via synergistic modulation of at least one extrinsic laryngeal muscle and at least one intrinsic laryngeal muscle.

BACKGROUND OF THE INVENTION

Thousands of people are unable to experience the simple pleasure of eating without the risk of life-threatening pneumonia and, consequently, suffer a significant reduction in their quality of life. Their inability to prevent foreign matter from entering the airway during swallowing, a condition referred to as aspiration, prohibits them from taking any food or liquid by mouth. Stroke is the most common cause of aspiration. Other causes of aspiration include traumatic brain injury, cerebral palsy. Parkinson's disease, multiple sclerosis, and other central nervous system disorders.

For these patients failing standard rehabilitation therapy, a percutaneous endoscopic gastronomy tube is the only safe form of nutrition. In extreme cases, these patients undergo surgical procedures that permanently separate the trachea from the esophagus, radically altering the throat. Such solutions can significantly reduce the patients' quality of life.

SUMMARY OF THE INVENTION

The present invention relates generally to a hybrid method for modulating upper airway function in a subject, and more particularly to a hybrid method for treating laryngeal disorders via synergistic modulation of at least one extrinsic laryngeal muscle and at least one intrinsic laryngeal muscle. The present invention provides an alternative therapeutic intervention that allows more normal alimentation while also protecting the airway and lungs from foreign matter and related consequential illness.

According to one aspect of the present invention, a hybrid method is provided for modulating upper airway function in a subject. The method comprises applying first and second therapy signals to the subject to modulate at least one extrinsic laryngeal muscle and at least one intrinsic laryngeal muscle to synergistically control laryngeal motion and vocal fold movement, respectively.

According to another aspect of the present invention, a hybrid method is provided for treating a laryngeal disorder in a subject. The method comprises applying first and second therapy signals to at least one extrinsic laryngeal muscle and a recurrent laryngeal nerve (RLN) to synergistically control laryngeal motion and vocal fold movement, respectively. Synergistic application of the first and second therapy signals promotes swallowing without aspiration in the subject.

According to yet another aspect of the present invention, a method is provided for treating laryngospasm in a subject. The method comprises administering a therapy signal to a RLN of the subject such that nerve conduction through the RLN is substantially blocked.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
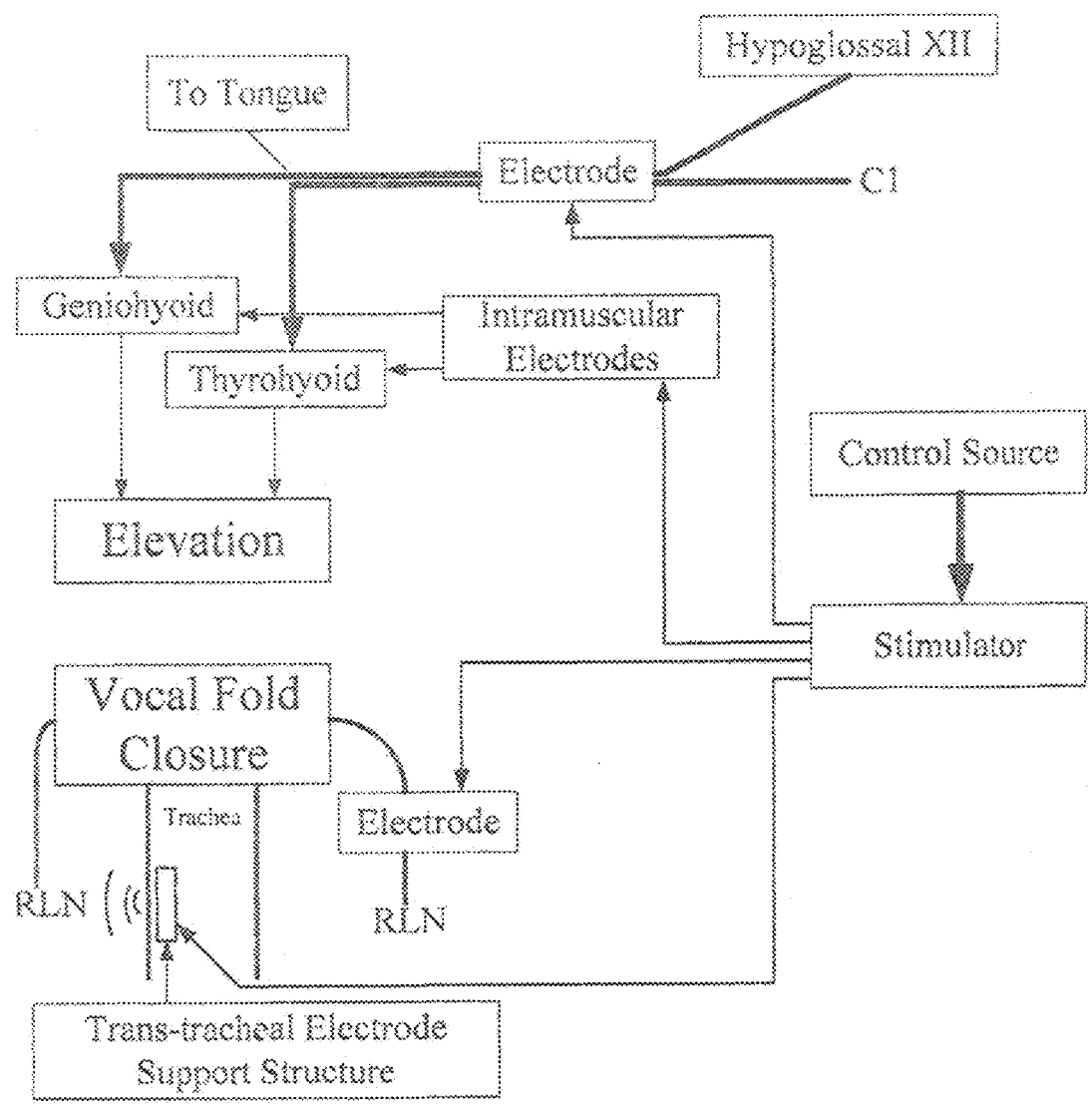
FIG. 1 is a schematic illustration showing a hybrid system for modulating upper airway function in a subject according to an aspect of the present invention.
Figure 2:
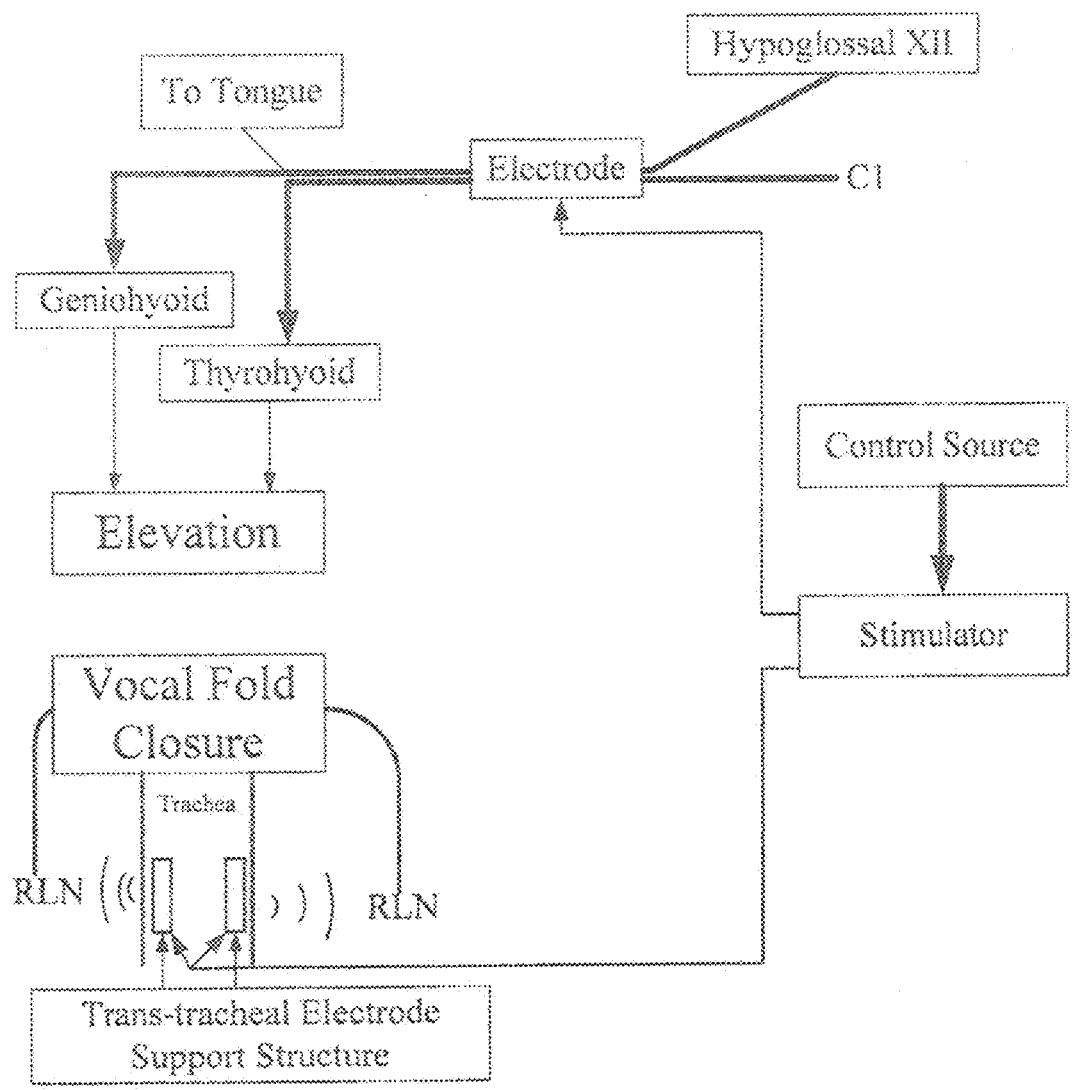
FIG. 2 is a schematic illustration showing a hybrid system for modulating upper airway function in a subject according to another aspect of the present invention.
Figure 3:
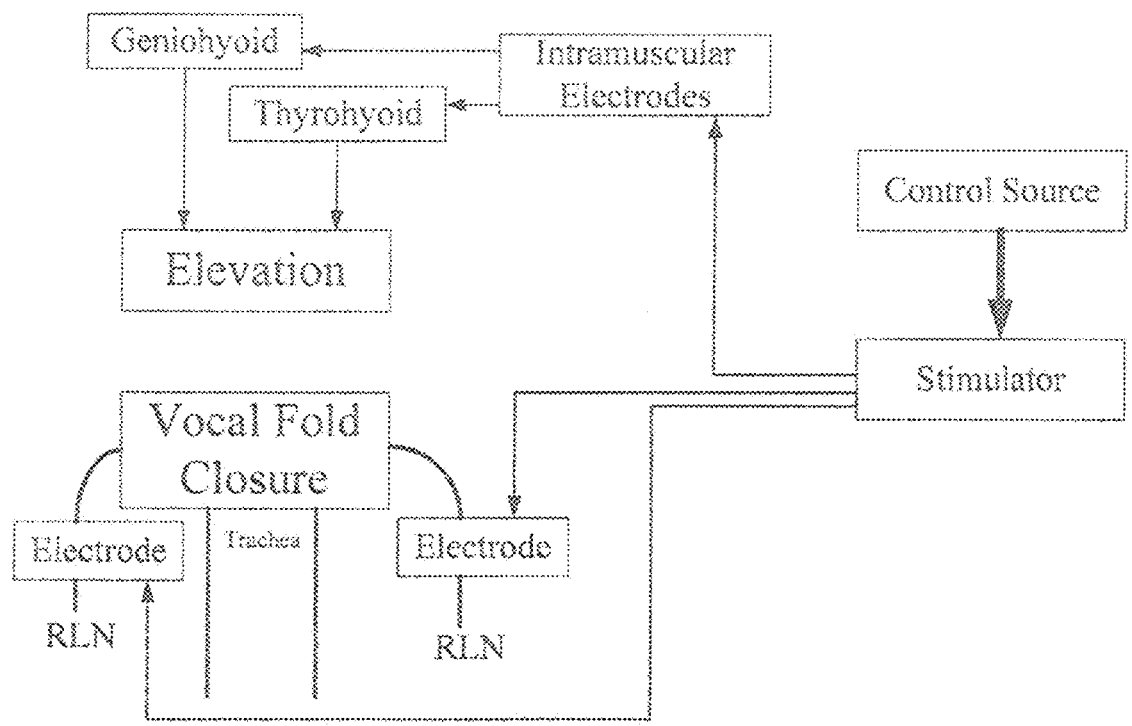
FIG. 3 is a schematic illustration showing a hybrid system for modulating upper airway function in a subject according to another aspect of the present invention.
Figure 4:
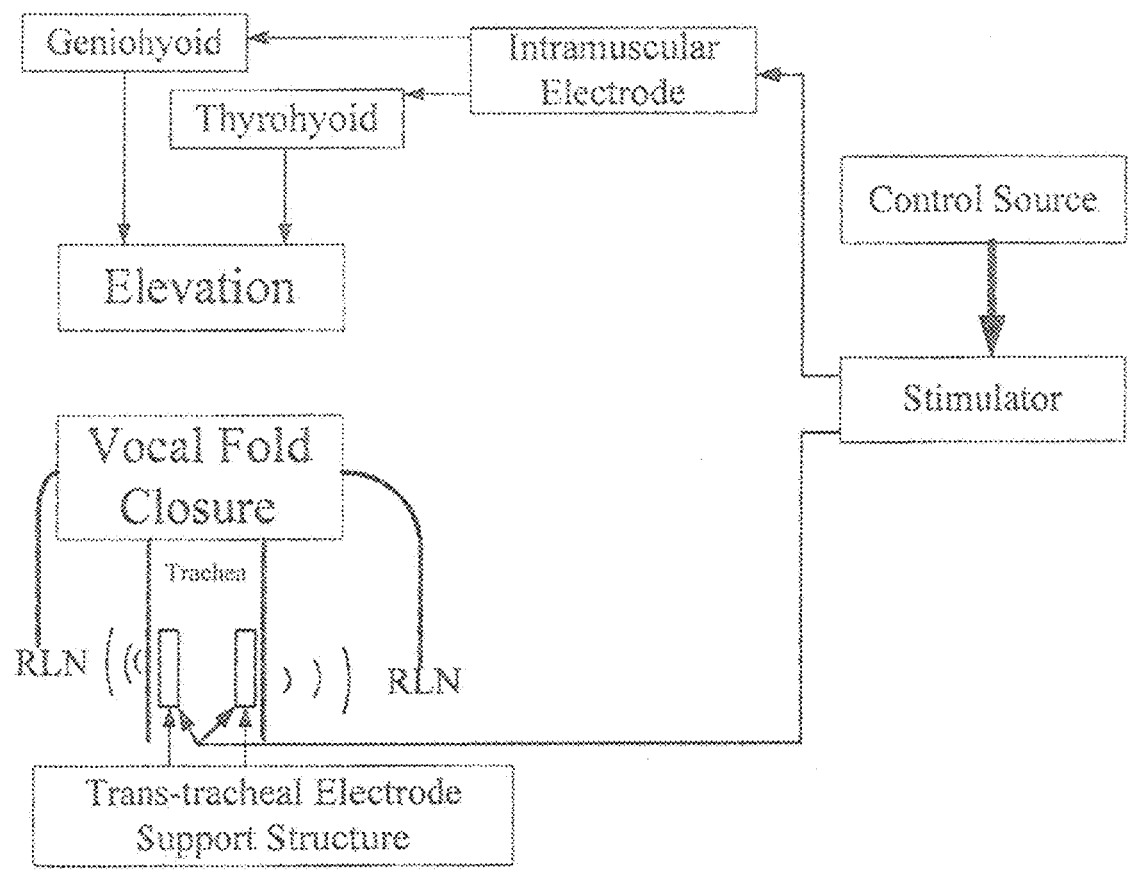
FIG. 4 is a schematic illustration showing a hybrid system for modulating upper airway function in a subject according to another aspect of the present invention.

Unless otherwise defined, all technical terms used herein have the same meaning as commonly understood by one of ordinary skill in the art to which the present invention pertains.

In the context of the present invention, the terms "modulate" or "modulating" can refer to causing a change in neuronal activity, chemistry, and/or metabolism. The change can refer to an increase, decrease, or even a change in a pattern of neuronal or muscle activity. The terms may refer to either excitatory or inhibitory stimulation, or a combination thereof, and may be at least electrical, magnetic, optical or chemical, or a combination of two or more of these. The terms "modulate" or "modulating" can also be used to refer to a masking, altering, overriding, or restoring of neuronal activity.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "upper airway disorder" can refer to a condition or disease in which there is a deviation from or interruption of the normal structure or function of the upper respiratory system, i.e., the nose, throat, larynx, and associated structures.

As used herein, the term "laryngeal disorder" can refer to a condition or disease in which there is a deviation from or interruption of the normal structure or function of the larynx.

As used herein, the term "treating" can refer to therapeutically regulating, preventing, improving, alleviating the symptoms of, and/or reducing the effects of an upper airway disorder (e.g., a laryngeal disorder).

As used herein, the term "electrical communication" can refer to the ability of an electric field generated by an electrode or electrode array to be transferred, or to have a neuromodulatory effect within and/or on at least one nerve, neuron, nervous tissue and/or muscle.

As used herein, the term "aspiration" can refer to penetration of food, liquid, and other foreign matter below the vocal folds.

Currently, it is unclear whether vocal fold closure or laryngeal motion (e.g., laryngeal motion) has the greatest effect in protecting proper upper airway function. Prior art methods for modulating upper airway function have evolved for electrically stimulating a single muscle group or nerve to separately control laryngeal motion or vocal fold movement without taking account of the relative contribution of each mechanism in protecting airway function. The present invention is based, at least in part, on the discovery that the mechanisms for laryngeal motion (e.g., laryngeal motion) and vocal fold movement do not operate separately and, rather, that the relative contribution of each mechanism is dependent on the etiology and condition of the subject. Based on this discovery, the present invention provides various hybrid approaches (FIGS. 1-4) for control upper airway function that combine muscle- or nerve-based modulation of at least one extrinsic laryngeal muscle and at least one intrinsic laryngeal muscle. This hybrid approach yields two synergistic actions, i.e., laryngeal motion and vocal fold movement to effectively modulate upper airway function.

Figure 5:
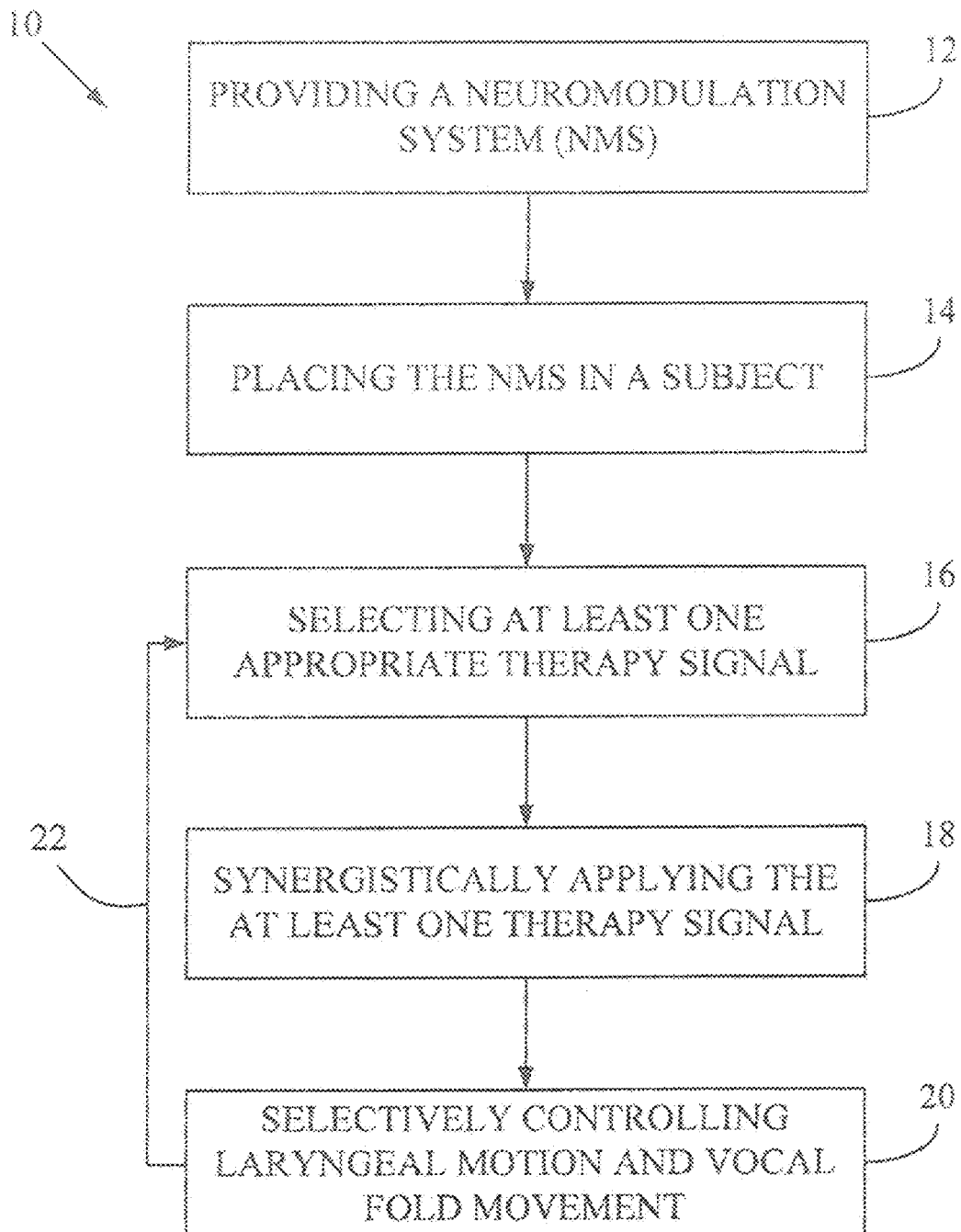
FIG. 5 is a process flow diagram illustrating a hybrid method for modulating upper airway function in a subject according to an aspect of the present invention.
Figure 6:
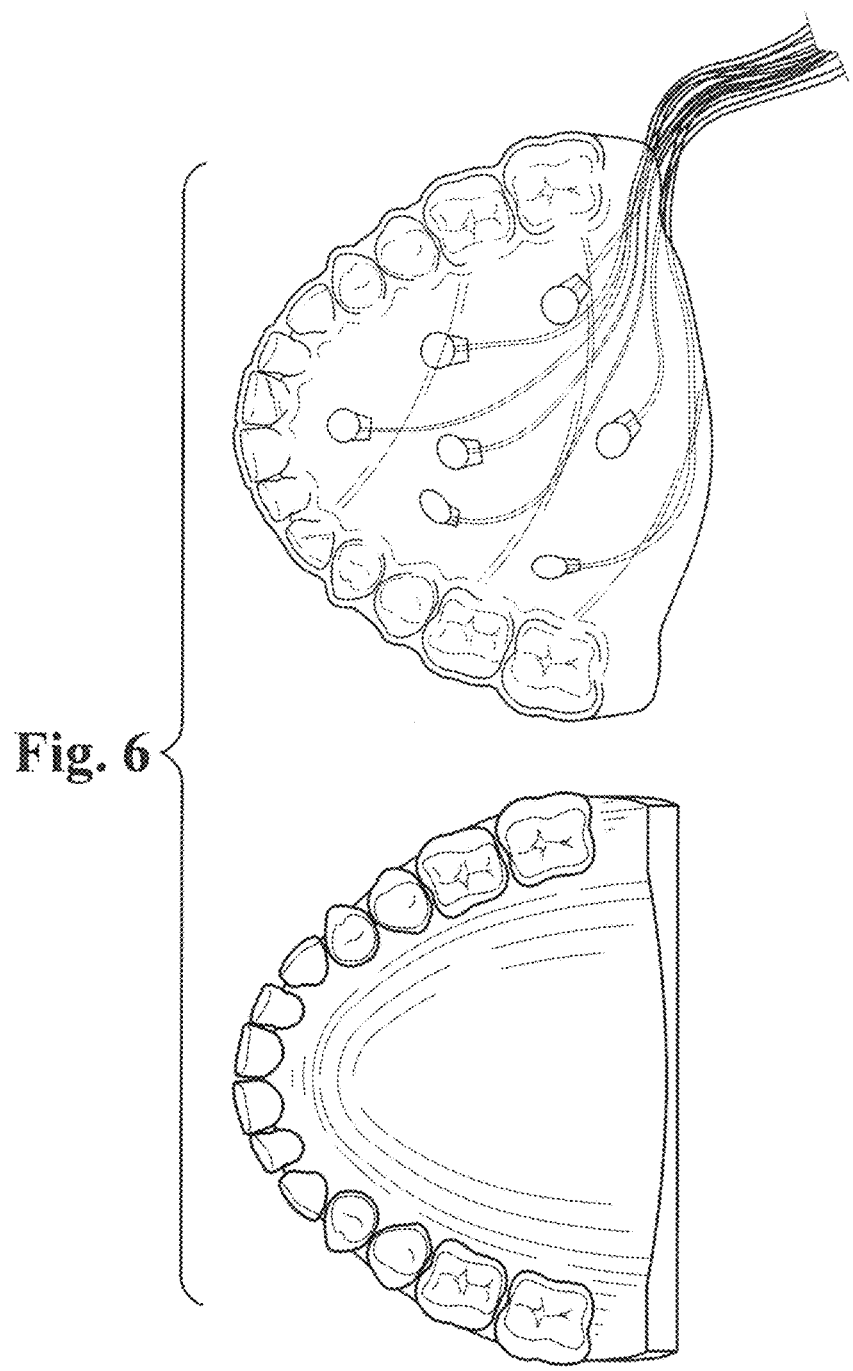
FIG. 6 is an image showing a dental appliance for detecting interoral pressure signals according to another aspect of the present invention.
Figure 7:
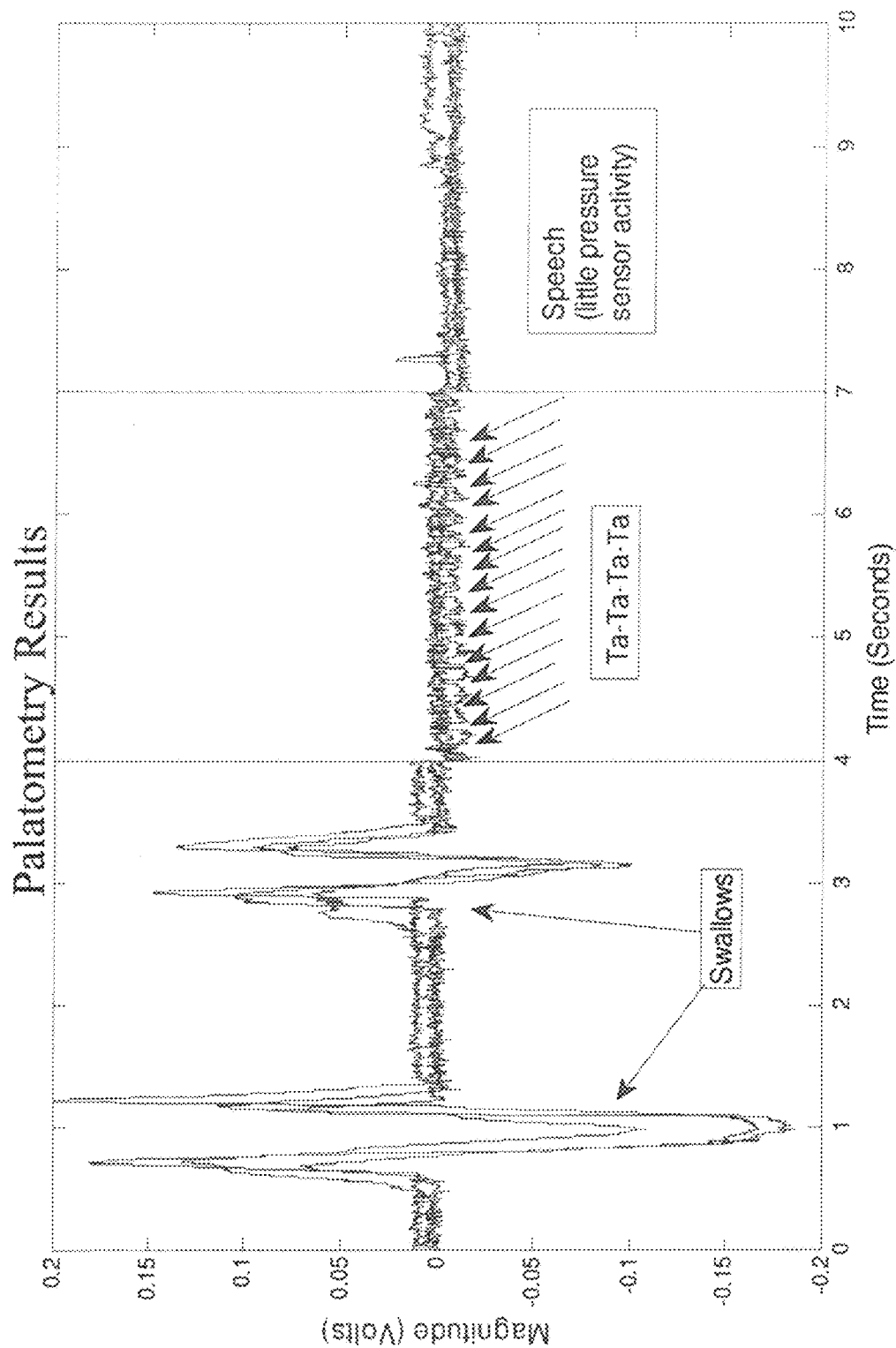
FIG. 7 is a plot comparing time (seconds) vs. magnitude (Volts) for the dental appliance in FIG. 6 when tested in five healthy subject and five dysphagic subjects.
Figure 8:
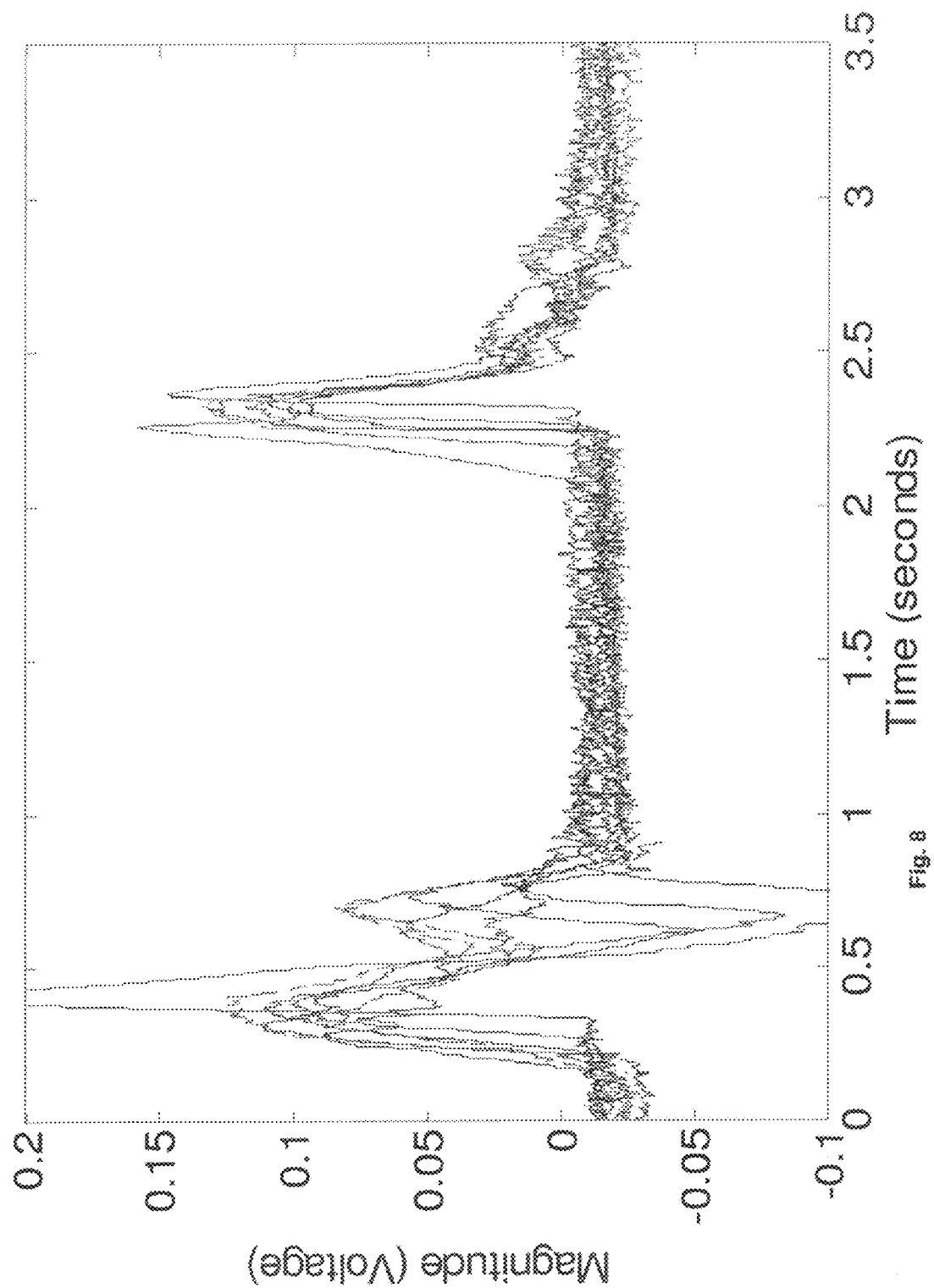
FIG. 8 is a plot comparing time (seconds) vs. magnitude (Volts) for the dental appliance in FIG. 6 and showing two common patterns (i.e., positive/negative vs. positive only)
Figure 9:
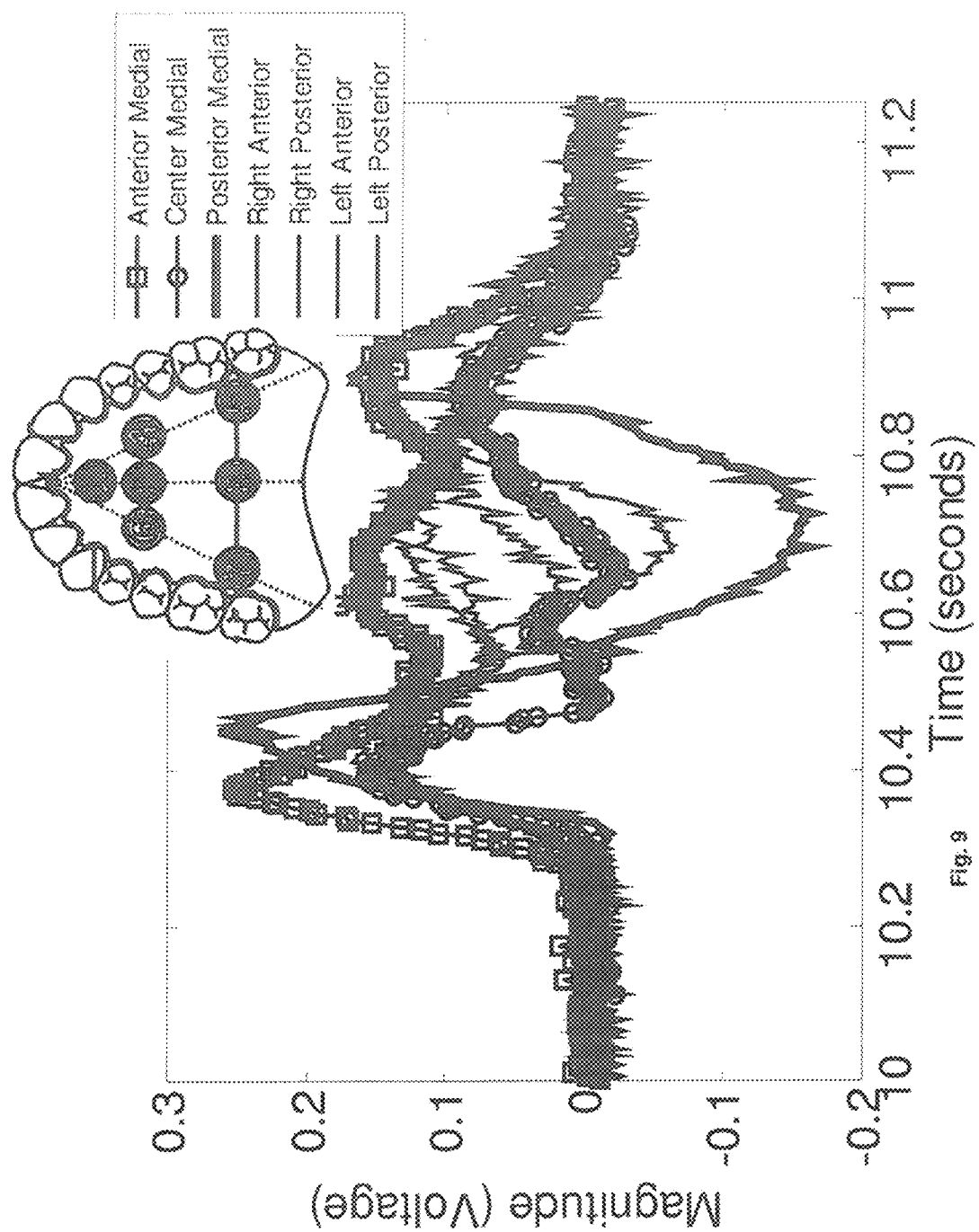
FIG. 9 is a plot comparing time (seconds) vs. magnitude (Volts) of the dental appliance in FIG. 6 showing the results of all seven sensors.
Figure 10:
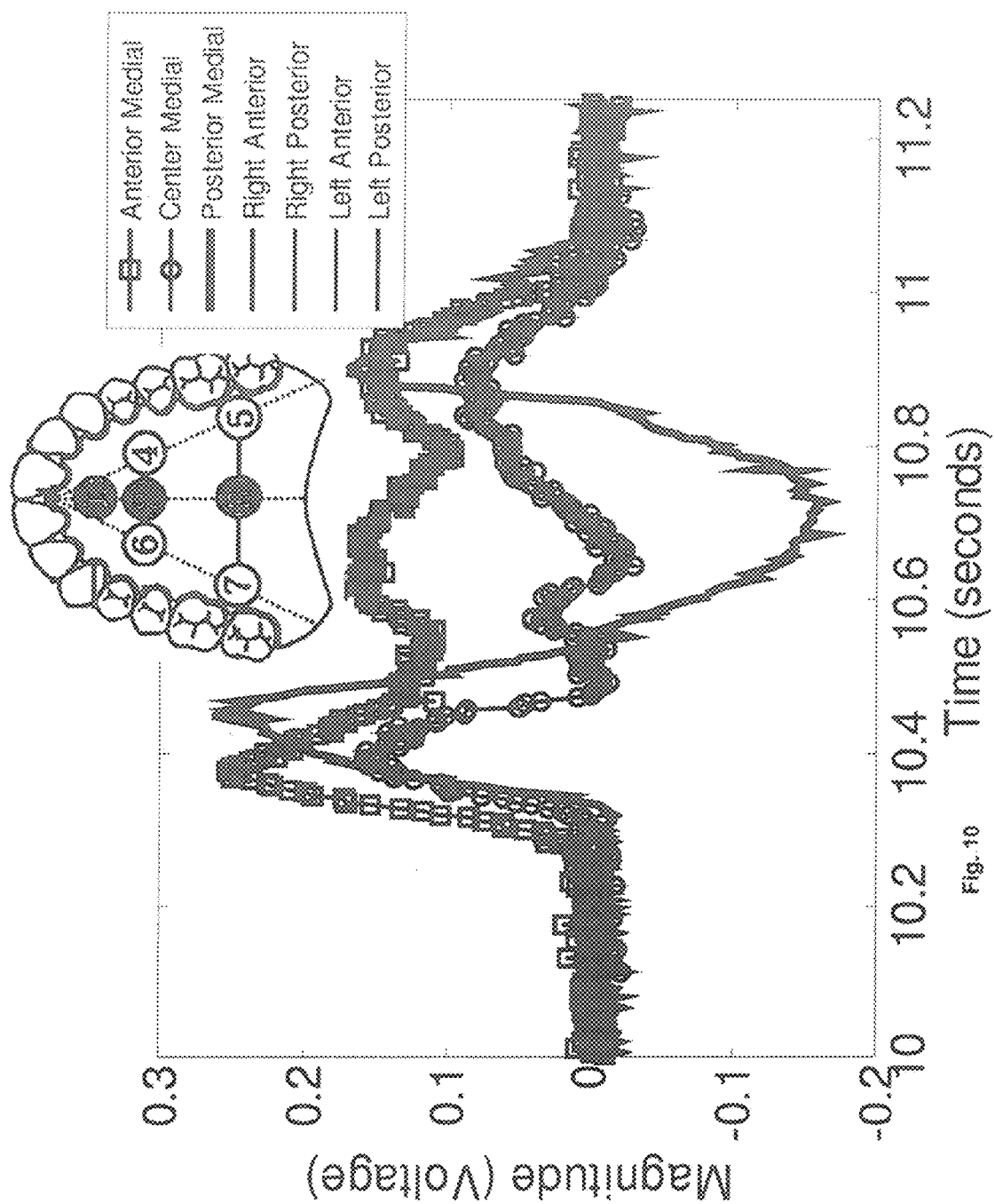
FIG. 10 is a plot comparing time (seconds) vs. magnitude (Volts) of the dental appliance in FIG. 6 showing the results of the three medial sensors.
Figure 11:
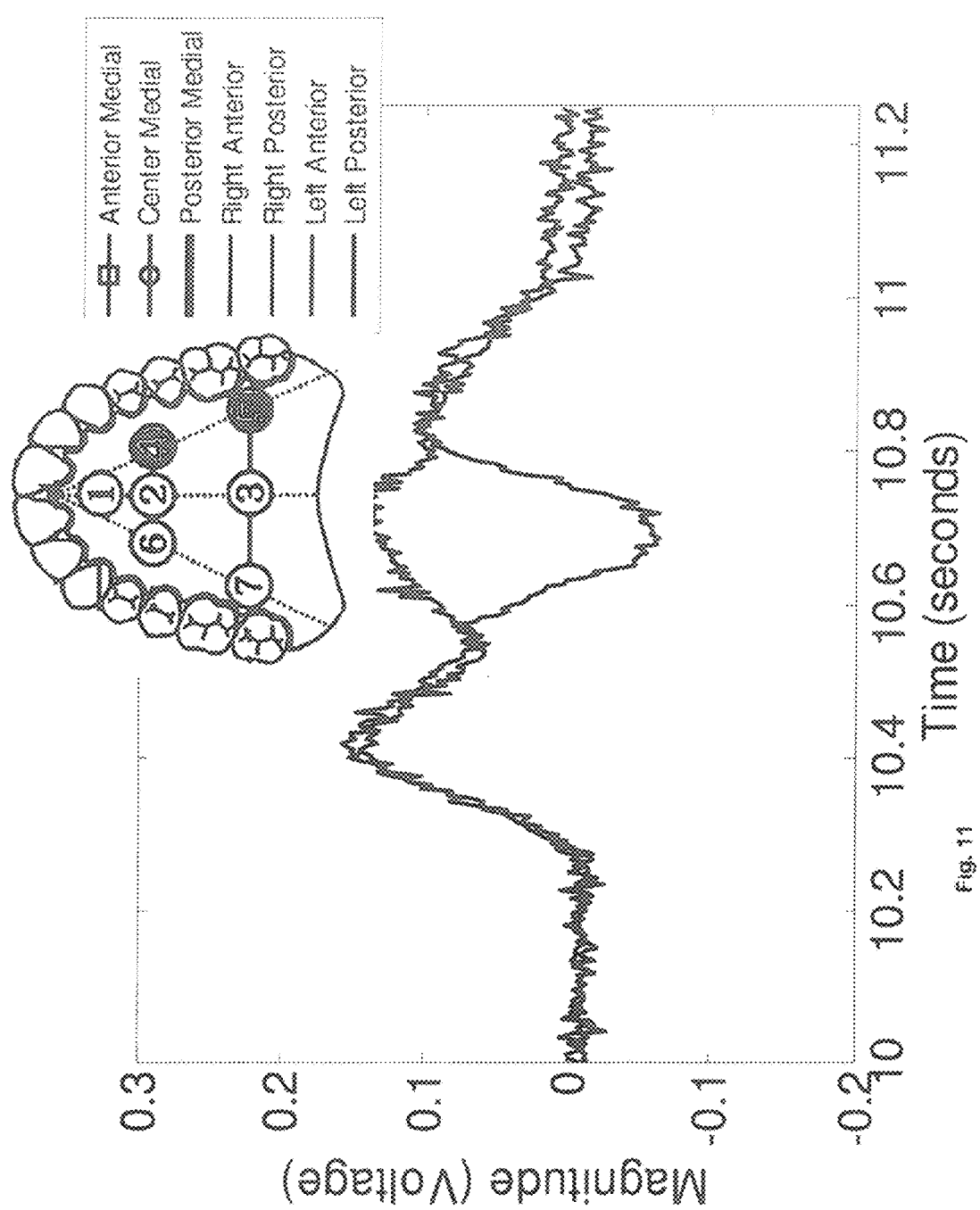
FIG. 11 is a plot comparing time (seconds) vs. magnitude (Volts) of the dental appliance in FIG. 6 showing the results of the right two sensors.
Figure 12:
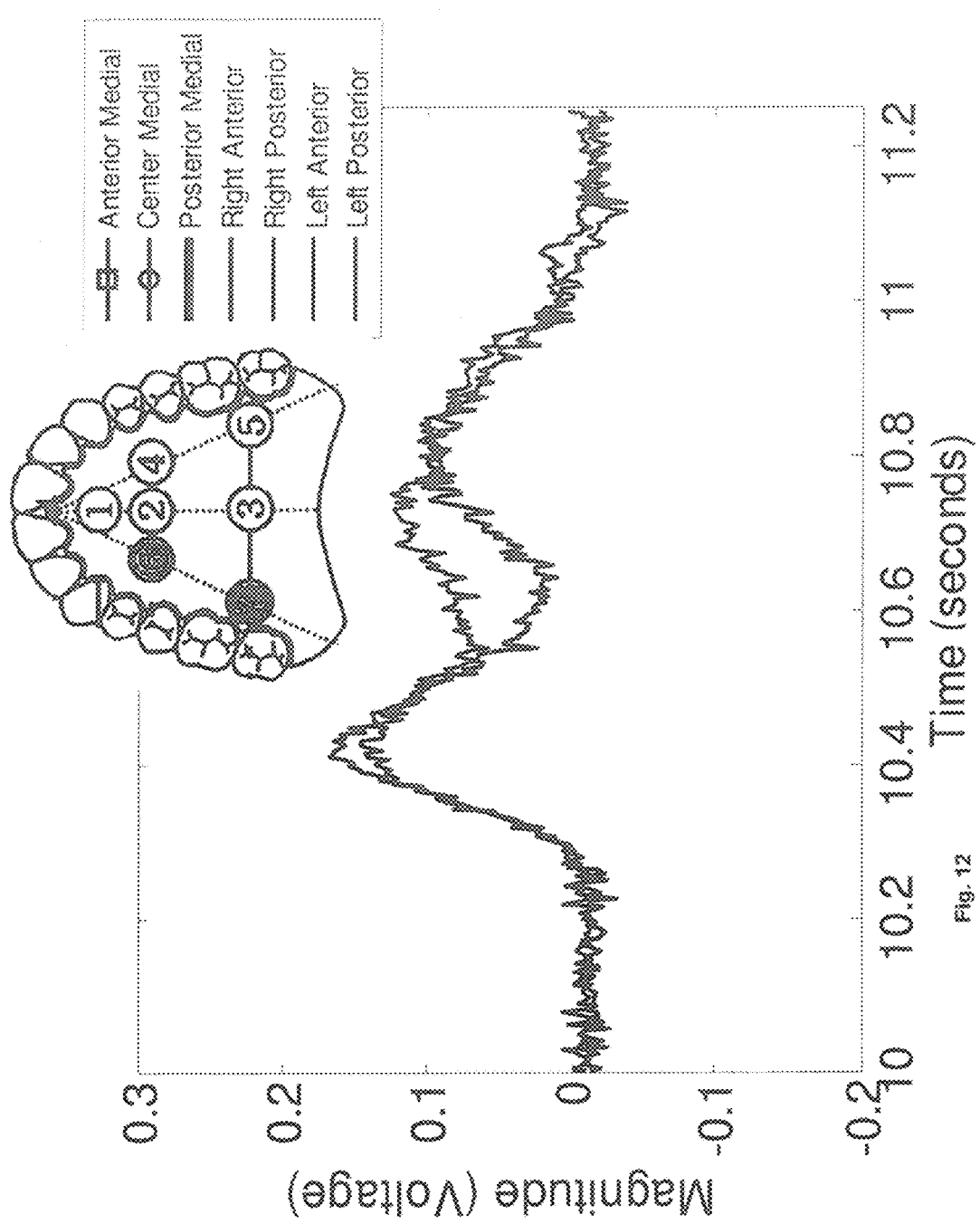
FIG. 12 is a plot comparing time (seconds) vs. magnitude (Volts) of the dental appliance in FIG. 6 showing the results of the left two sensors.
Figure 13:
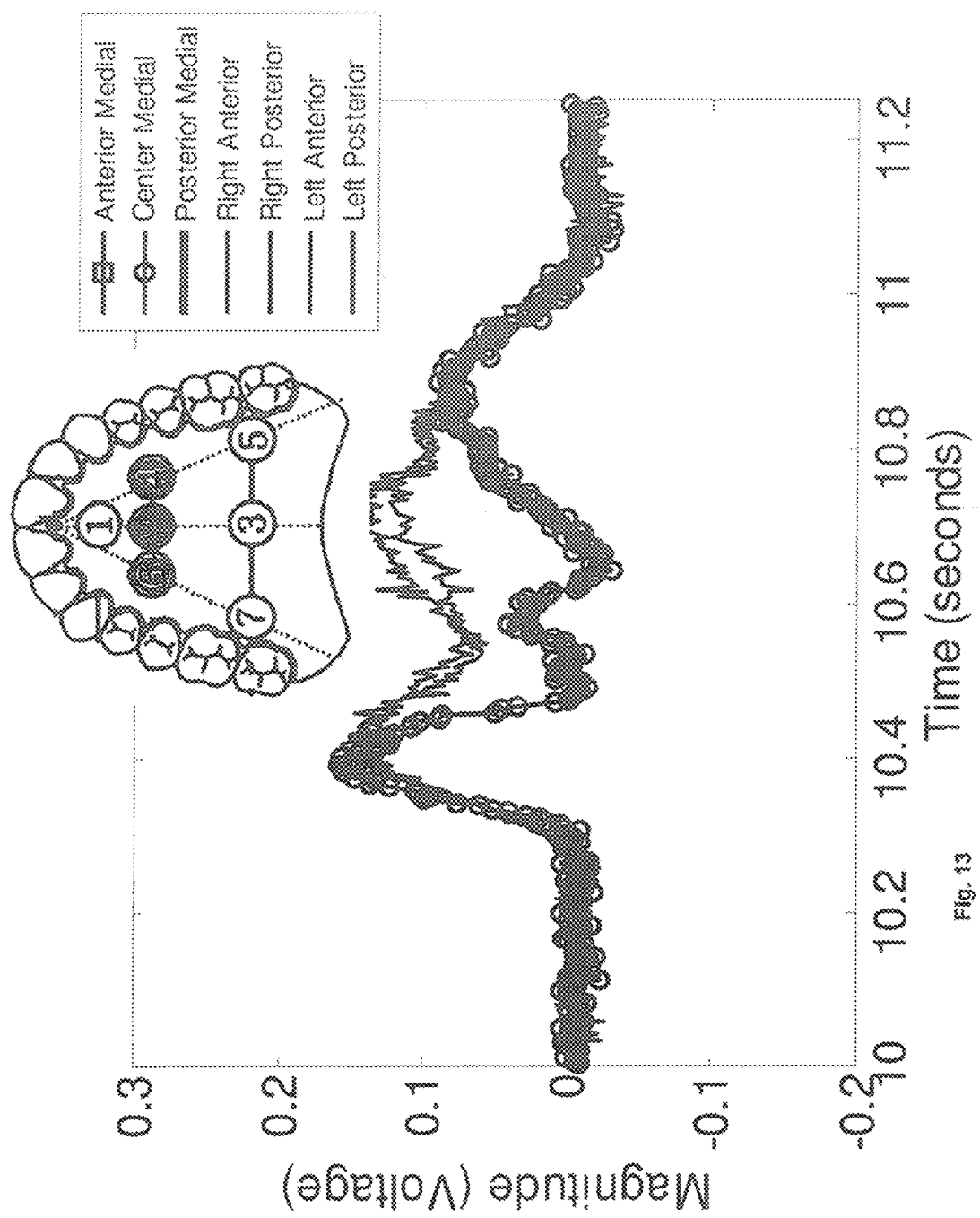
FIG. 13 is a plot comparing time (seconds) vs. magnitude (Volts) of the dental appliance in FIG. 6 showing the results of the central row of sensors.
Figure 14:
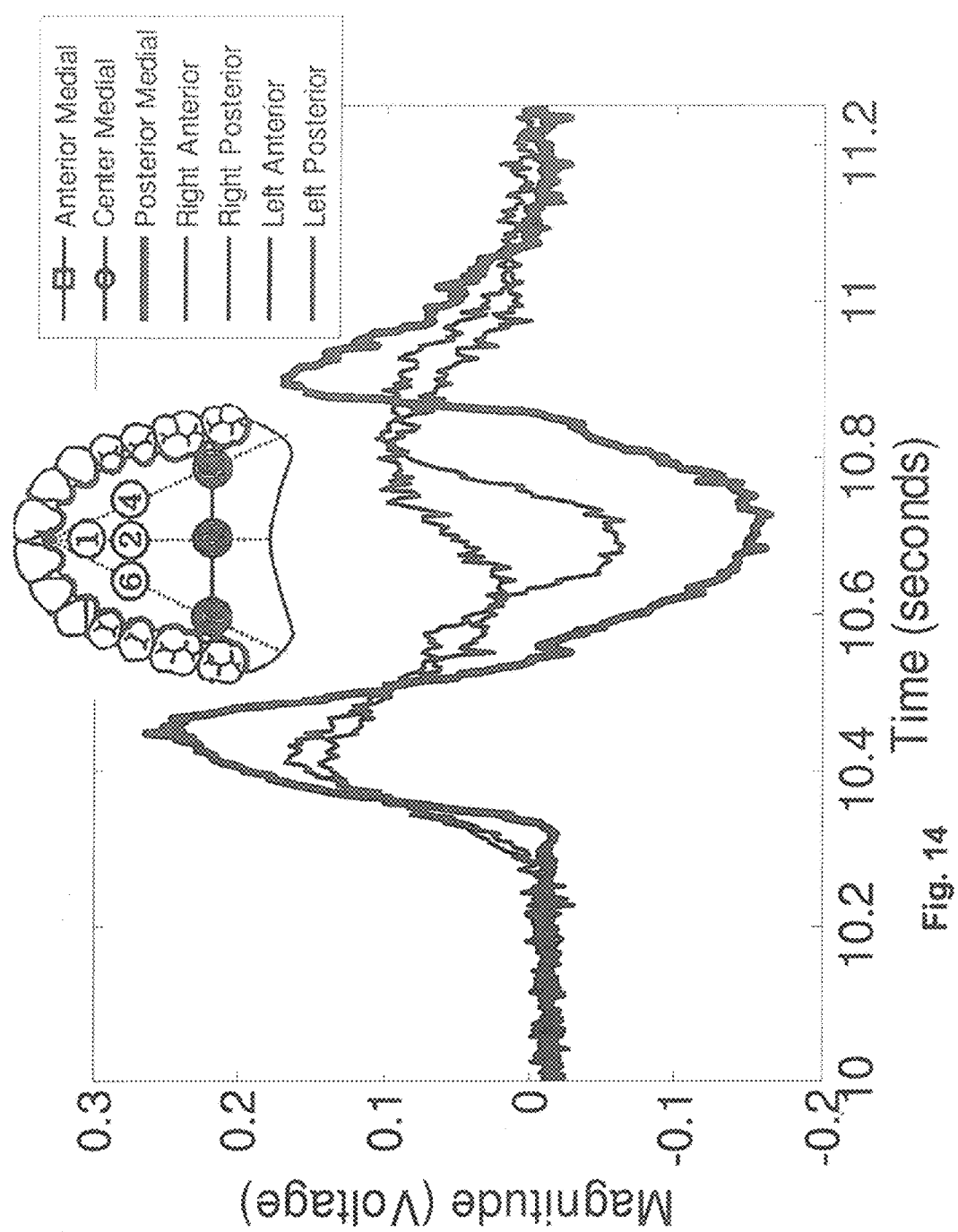
FIG. 14 is a plot comparing time (seconds) vs. magnitude (Volts) of the dental appliance in FIG. 6 showing the results of the three posterior sensors.

As shown in FIG. 5, one aspect of the present invention includes a method 10 for modulating upper airway function in a subject. Although the method 10 is illustrated below in terms of modulating upper airway function to treat aspiration, it will be appreciated that the present invention can be used to treat a variety of upper airway disorders, such as other forms of laryngeal, oral, vocal fold (e.g., dysphonia), and esophageal dysfunction.

The method 10 includes providing a neuromodulation system at Step 12. The neuromodulation system is configured to control upper airway function by synergistically modulating laryngeal motion and vocal fold movement. The neuromodulation system can include a controller (or control source), a signal generator, an electrode array, a sensor array, and a power source. Various components of the neuromodulation system can be maintained in a housing (e.g., a pacemaker "can") with an optional external switch or sensor for activating the neuromodulation system. The various components of the neuromodulation system can communicate with one another via a variety of mechanisms, such as direct electrical communication, RF communication, magnetic communication, optical communication, sonic communication, and combinations thereof.

The neuromodulation system can be portable and adapted to be borne by a subject suffering from an upper airway disorder for a desired period of time. For example, the neuromodulation system can be borne by a subject for an acute period of time (e.g., during an emergency situation), for a semi-chronic period of time (e.g., less than about a week to about 6 weeks), or for a chronic period of time (e.g., greater than about 6 weeks). The controller, the signal generator, the electrode array, the sensor array (where applicable), and/or the power source can be provided as separate and distinct components, as partially integrated components, or as fully integrated components. For example, the neuromodulation system can include one or more integrated electrodes having processing, signal generating, external communicating, and/or sensing capabilities, one or more of which are fully or partially integrated into the integrated electrode(s), such as a BION microstimulator (Boston Scientific Neuromodulation Corp., Valencia, Calif.).

The controller can include a microprocessor, a hardwired circuit, or other appropriate means for controlling various aspects of the neuromodulation system. For example, the controller can operate the signal generator and/or receive information from various sources, such as the sensor array. The controller can be adapted to store a stimulation program (or programs) and operate the signal generator according to the stimulation program(s). Stimulation programs can include predetermined, set programs (e.g., hardwired into the controller) and adaptive, dynamic programs (e.g., software that adapts an artificial stimulation pattern according to various inputs, such as input from the sensor array). The controller can select between various programs and/or actively modify a stimulation program according to various inputs, such as information received from a subject, information received from the sensor array, information received from the signal generator, information received from the electrode array, information received from a remote processor, and/or information received from a health care professional.

The signal generator is configured to provide one or more therapy signals to the electrode array. The therapy signals can communicate stimulating energy, such as electrical current pulses to the electrode array to modulate upper airway function. The signal generator can optionally include circuitry and/or other implantable components for outputting electrical pulses through electrical leads to the electrode array and/or communicate power to the electrode array via mechanisms other than electrical connection (e.g., RF power transmission and/or magnetic power transmission).

Signals from the signal generator can additionally or optionally be communicative in nature, for example, communicating stimulation program information, subject information, and other types of information. The signal generator can include an RF transmitter communicating with a self-contained electrode acting as a receiver, i.e., an electrode that is not physically "wired" to a separate signal generator via electrical leads or other means. For example, a self-contained electrode can receive the RF transmission as a source of power and/or as a control signal for timing delivery of a therapy signal.

The electrode array can include one or more electrodes, such as a first electrode configured to apply a first therapy signal to a muscle (or one or more nerves innervating the muscle) and a second electrode adapted to apply a second therapy signal to a second different muscle (or one or more nerves innervating the second muscle). In one example of the method 10, the first electrode can be placed in electrical communication with at least one extrinsic laryngeal muscle via subcutaneous placement, percutaneous placement, intramuscular placement, and/or exterior placement on the muscle surface. Alternatively, the first electrode can be placed in electrical communication with at least one nerve that innervates the at least one extrinsic laryngeal muscle. The second electrode can be placed in electrical communication with one or more nerves capable of controlling vocal fold movement, such as the left and/or right RLN, the vagus nerve ($X^{th}$ Cranial Nerve), the hypoglossal nerve ($XII^{th}$ Cranial Nerve), the trigeminal nerve ($V^{th}$ Cranial Nerve), and/or the cervical spinal nerve C1 (suboccipital nerve), via subcutaneous and/or percutaneous placement. Alternatively, the second electrode can be placed in electrical communication with at least one intrinsic laryngeal muscle via subcutaneous placement, percutaneous placement, intramuscular placement, and/or exterior placement on the muscle surface.

The electrode array can include one or more of the following types and/or categories of electrodes: epimysial electrodes; intramuscular electrodes, such as Peterson electrodes; nerve cuff electrodes; self-contained electrodes; monopolar electrodes; bipolar electrodes; multi-contact electrodes; and/or other known electrode types/categories and combinations thereof. It will be appreciated that the electrode array can additionally or optionally include one or more associated flexible, extensible electrical leads.

In one example of the present invention, one or more of the electrodes comprising the electrode array can comprise a spatially-selective electrode, such as the flat interface nerve electrode (FINE) disclosed in U.S. Pat. No. 6,456,866, the entirety of which is hereby incorporated by reference. To date, there is limited selectivity in spiral and other types of electrodes. In fact, only quasi-trapezoidal pulsing schemes using anodal blocking for size-selective recruitment have been used to selectively stimulate the different axons in the RLN based on differences in fiber diameter. Additionally, intrafascicular electrodes have shown selectivity, but not clear safety in clinical applications. The use of a FINE electrode to deliver a therapy signal to the RLN, for example, can permit selective activation of different intrinsic laryngeal muscles (i.e., spatial selectivity) based on any somatotopic organization within the RLN.

The sensor array can include one or more sensors for detecting a physiological parameter of interest, such as force, movement, pressure, position, displacement, myoelectrical activity, and/or nerve conduction or neuroelectrical activity. The sensor array can also include one or more sensors adapted for subcutaneous use, exterior placement (e.g., skin or hair), and/or percutaneous placement. Further examples of sensors and systems (e.g., open- and closed-loop systems) formed therewith are provided below. It should be appreciated that one or more electrodes of the electrode array can also serve as a sensor in the sensor array.

At Step 14, all or only a portion of the neuromodulation system is placed in the subject. Prior to placement, however, at least one extrinsic laryngeal muscle (e.g., anterior or posterior digastric muscles, geniohyoid muscle, stylohyoid muscle, thyrohyoid muscle, sternohyoid muscle), at least one intrinsic laryngeal muscle, and/or the recurrent laryngeal nerve (RLN) (left or right RLN) can be identified using visual confirmation, an imaging modality (e.g., MRI or CT), and/or selective neurostimulation techniques. Using neurostimulation, for example, an electrical current can be briefly delivered to at least one extrinsic or intrinsic laryngeal muscle to ensure proper placement of the electrode array. Similarly, an electrical current can be briefly delivered to the RLN to ensure proper placement of the electrode array.

Placement of the neuromodulation system can include disposing the controller, the signal generator, and the power source in a housing as a single unit. The housing can then be placed in a subcutaneous pocket (e.g., formed in the upper chest) of the subject. Alternatively, the controller, signal generator, and/or power source can be left external to the subject where, for example, the electrode array includes self-contained electrodes. One or more external devices, such as a hand switch can be optionally connected to the controller or otherwise placed in communication therewith for subject-controlled or open-loop upper airway modulation (described in greater detail below).

Placement of the neuromodulation system can also include placing one or more electrodes of the electrode array into electrical communication with at least one extrinsic laryngeal muscle, at least one nerve that innervates the at least one extrinsic laryngeal muscle, at least one intrinsic laryngeal muscle, and/or at least one nerve that innervates the at least one intrinsic laryngeal muscle (e.g., the left and/or right RLN). For example, a first electrode can be placed into electrical communication with at least one extrinsic laryngeal muscle by fixing the first electrode to a surface of the extrinsic laryngeal muscle or by inserting the first electrode into the extrinsic laryngeal muscle. Additionally, a second electrode can be placed into electrical communication with the RLN (left and/or right) by fixing the second electrode to a select portion of the RLN. If it has not been done so already, the first and second electrodes can then be placed in communication with the power source (e.g., via direct electrical connection).

Alternatively, placement of the neuromodulation system can include placing one or more electrodes (e.g., the FINE) into electrical contact with at least one nerve that innervates an extrinsic laryngeal nerve, such as the hypoglossal nerve, the C1 nerve, the junction formed by the hypoglossal nerve and the C1 nerve, and/or branches thereof. Placement of an electrode at or downstream of the hypoglossal nerve/C1 nerve junction may be useful for modulating one or more of the geniohyoid and thyrohyoid muscles. Alternatively, placement of an electrode in electrical communication with a branch from the hypoglossal nerve/C1 nerve bundle may be useful for modulating one or more of the infrahyoidal muscles, such as the sternohyoid, sternothyroid, and omohyoid muscles.

The sensor array can be placed either before, during, or after placement of the electrode array. The sensor array can be in communication with any of the components of the neuromodulation system, including an electrical lead or leads. The sensor array can be secured (e.g., using an adhesive, suture, bone anchor, or other means) at an exterior or interior location in or on the subject's body so that a physiological parameter of interest can be detected. Non-limiting examples of bodily locations upon or in which the sensor array can be secured include the hyolaryngeal complex, the hyoid bone, the epiglottis, any of the laryngeal cartilages (e.g., a thyroid cartilage, a cricoid cartilage, an arytenoid cartilage, a cuneiform cartilage, and/or a corniculate cartilage), the upper esophageal sphincter, the oral cavity, in or over the ear canal, the nasalis muscle, a muscle or muscles associated with facial expression (e.g., the orbicularis oris, orbicularis oculi, masseter, zygomaticus major, frontalis), the superior laryngeal nerve, the submandibular nerve, the lingual nerve, and/or the glossopharyngeal nerve.

It should be appreciated that the sensor array can additionally or optionally include at least one sensor positioned on or integrated with an implantable or wearable device or appliance. Non-limiting examples of such devices or appliances can include feeding utensils, drinking vessels, rings or other hand-worn articles, dental appliances (e.g., oral retainers), and clothing accessories.

Following placement of the neuromodulation system, at least one appropriate therapy signal is selected at Step 16. The therapy signal can comprise one or more electrical signals capable of modulating at least one extrinsic laryngeal muscle, at least one nerve that innervates the at least one extrinsic laryngeal muscle, at least one intrinsic laryngeal muscle, and/or at least one nerve that innervates the at least one intrinsic laryngeal muscle (e.g., the right and/or left RLN) of a subject. The therapy signal can have a desired strength and timing that is based on a variety of considerations, such as the location of the neuromodulation system, the overall health of the subject (e.g., external or internal), the particular upper airway disorder from which a subject is suffering, the severity of the upper airway disorder, any co-existing morbidities, and/or current medication dosage by the subject. In a subject suffering from aspiration, for example, first and second therapy signals can be selected so that synergistic control of laryngeal motion and vocal fold movement is possible.

At Step 18, the at least one appropriate therapy signal is applied to at least one extrinsic laryngeal muscle, at least one nerve that innervates the at least one extrinsic laryngeal muscle, at least one intrinsic laryngeal muscle, and/or at least one nerve that innervates the at least one intrinsic laryngeal muscle (e.g., the right and/or left RLN) to synergistically control laryngeal motion and vocal fold movement (respectively). The therapy signal can be delivered to one or more of the electrodes comprising the electrode array either continuously, periodically, episodically, and/or a combination thereof. For example, the therapy signal can be delivered in a unipolar, bipolar, and/or multipolar sequence or, alternatively, via a sequential wave, charge-balanced biphasic square wave, quasi-trapezoidal, sine wave, or any combination thereof. The therapy signal can be delivered to the electrode array all at once or, alternatively, to only a select number of electrodes comprising the electrode array.

The particular voltage, current, and frequency of the therapy signal may be varied as needed. For example, the therapy signal can be delivered to the electrode array at a desired voltage (e.g., at about 0.1 v to about 25 v), at a desired current (e.g., at about 1 microamp to about 50 milliamps), at a desired frequency (e.g., at about 0.5 Hz to about 10,000 Hz), and at a desired pulse-width (e.g., at about 5 μsec to about 10,000 μsec).

At Step 20, the neuromodulation system can be activated to selectively control laryngeal motion and vocal fold movement. The stimulation parameters of the therapy signal(s) (e.g., timing, frequency, voltage, etc.) can be varied as needed so that extrinsic laryngeal muscle function and intrinsic laryngeal muscle function (via RLN stimulation, for example) are synergistically controlled. This, in turn, causes each mechanism to contribute to improving upper airway function. For example, the stimulation parameters of a first therapy signal can be optimized to promote motion (e.g., elevation) of the hyolaryngeal complex by directly stimulating a single one of the hyoglossus, the posterior belly of the digastric, or the stylohyoid muscles. Additionally, the stimulation parameters of a second therapy signal can be optimized to promote vocal fold closure. For example, delivery of the second therapy signal (in combination with the first therapy signal) can be optimized to avoid or minimize non-selective stimulation of one or more of the axons comprising the RLN, which can result in improper timing of vocal fold movement (e.g., closure) and thus interfere with certain stages of swallowing.

As noted above, the stimulation parameters of the therapy signal(s), and in particular the timing of the therapy signal(s) can be optimized so that extrinsic laryngeal muscle function and vocal fold movement are synergistically controlled. For example, a therapy signal (or signals) can be delivered to at least one intrinsic laryngeal muscle or a nerve(s) that innervate the at least one intrinsic laryngeal muscle (e.g., the right and/or left RLN) either prior to, contemporaneous with, or after delivery of a therapy signal (or signals) to an extrinsic laryngeal muscle. Alternatively, a therapy signal (or signals) can be delivered to an extrinsic laryngeal muscle and/or a nerve that innervates the at least one extrinsic laryngeal muscle either prior to, contemporaneous with, or after delivery of a therapy signal (or signals) to at least one intrinsic laryngeal muscle (e.g., the right and/or left RLN). In one example of the present invention, delivery of a therapy signal (or signals) to an extrinsic laryngeal muscle may be done over the entire swallow cycle, while delivery of another therapy signal (or signals) to the right and/or left RLN (i.e., to promote vocal fold closure) can be done at a particular moment during bolus passage to mitigate or prevent an upper airway disorder (e.g., aspiration).

At Step 22, the neuromodulation system can be operated as either an open- or closed-loop system to promote upper airway function in a subject. In an open-loop system, a medical professional or the subject may, at any time, manually or by the use of pumps, motorized elements, etc. adjust therapy signal parameters (e.g., pulse-amplitude, pulse-width, pulse-frequency, or duty cycle). An open-loop system can be initiated in response to a subject prompt (e.g., during feeding) via an external switch or sensor, such as a hand switch or via voice command, motion sensor, or one or more of the sensors of the sensor array, which can be "wired" or otherwise in communication with the neuromodulation system.

Generally, open-loop systems of the prior art include devices that are activated by an external button located on the device or by a hand switch held by the subject. Open-loop systems of the present invention, however, can include user interfaces and controls that integrate and mimic a more natural part of swallowing and feeding activities. For example, open-loop systems of the present invention can include one or more buttons located on feeding utensils or drinking vessels. The button(s) may be in communication with the neuromodulation system via wireless communication, for example, to make operation of the button(s) more convenient.

Alternatively, open-loop systems of the present invention can include an RFID and/or other short-range wireless communication means (e.g., on feeding utensils or drinking vessels) and a detector (or detectors) located near or in a subject's oral cavity. In this system configuration, the process of taking a bite of food may be detected automatically when the food is placed in the subject's mouth. The detector(s) can then indicate the type of utensil (e.g., fork or glass) and other characteristics to optimize stimulation patterns for a particular type of food (e.g., oatmeal versus water). Alternatively, the short-range communicator could be located on a ring or other hand-worn device that simply indicates approximation of the hand to the mouth. One or more detectors can then be located on a retainer or other similar appliance (e.g., glasses, earring, necklace, etc.), which can be placed in the mouth and calibrated to record an eating event.

Still another variation of an open-loop system can include a tongue and/or other cranial-located switch or sensor. For example, at least one switch can be placed in the mouth of a subject (e.g., as part of a retainer) and activated by the tongue when the subject tries to swallow. A variation of the tongue switch can include a tooth switch that is activated by a particular bite pattern (e.g., two taps of the teeth), which is not mistaken for the act of chewing. Alternatively, one or more sensors could be used to detect the activity (e.g., EMG) of certain facial muscles so that deliberate activation of these muscles serves as a stimulation command source.

The neuromodulation system can also function as a closed-loop system so that the strength and timing of at least one therapy signal can be altered in response to a physiological parameter of interest. For example, delivery of a therapy signal (or signals) can be initiated, modified, or otherwise adapted according to a sensor input (i.e., a physiological parameter of interest) received by the controller. The sensor array can include one or more sensors configured and placed subcutaneously and/or intramuscularly to provide physiologically-relevant feedback to the neuromodulation system. Such feedback can then be used to drive delivery of at least one therapy signal to a select extrinsic laryngeal muscle and/or the RLN as measured via the feedback.

Figure 15:
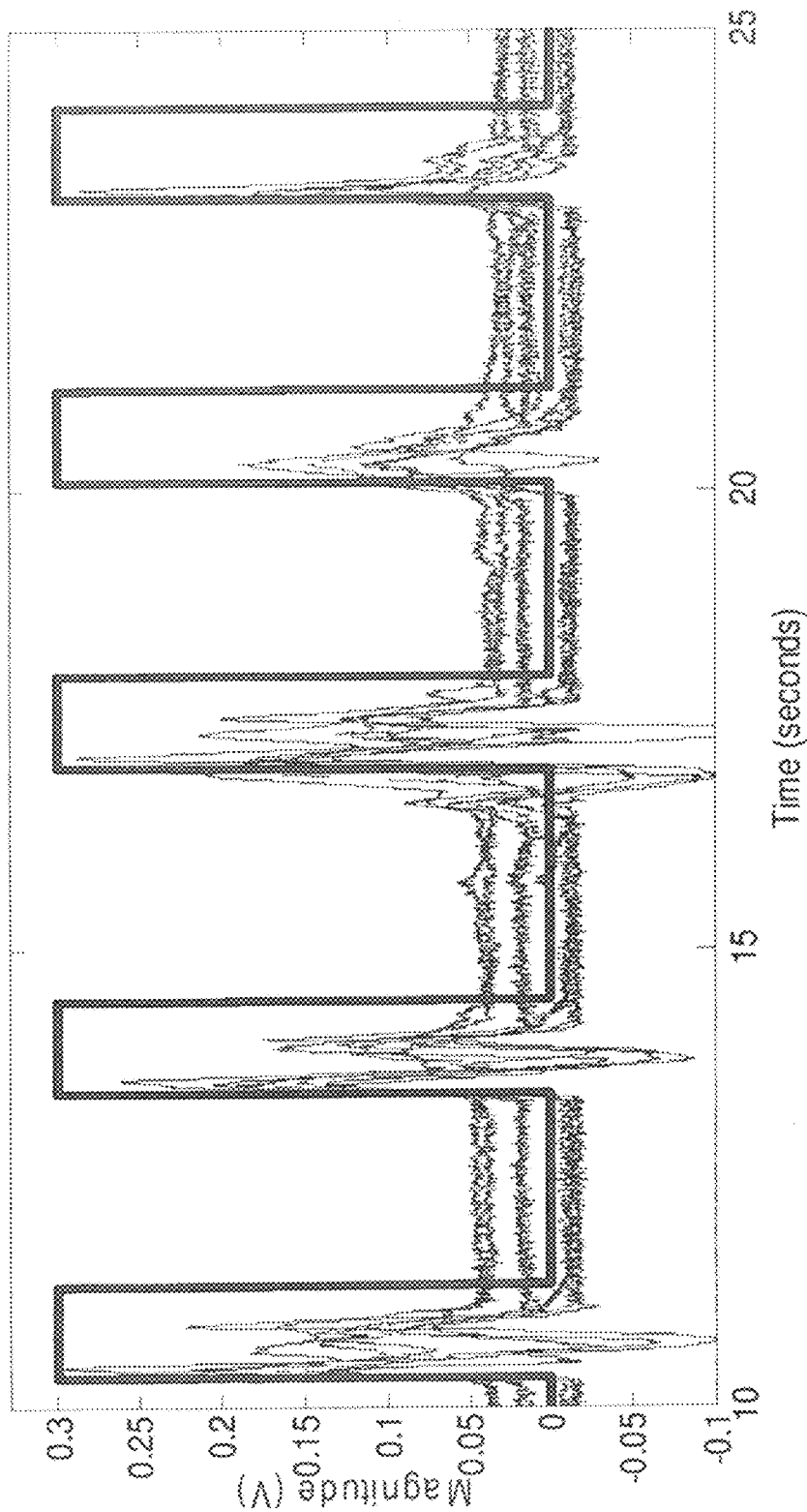
FIG. 15 is a plot comparing time (seconds) vs. magnitude (Volts) of the dental appliance in FIG. 6 showing the results of a swallow recognition algorithm according to another aspect of the present invention.

It will be appreciated that the present invention can include a variety of closed-loop system configurations for modulating upper airway function in a subject in response to a physiological parameter of interest. Non-limiting examples of sensor and physiological parameter of interest can include:

(a) submental EMG sensor(s)—using one or more sensors to detect the EMG of muscles in the submental region to control tongue movement, which is useful in chewing and swallowing processes;

(b) palatal tongue pressure sensor(s)—a swallow is normally initiated by pressing the tongue against the hard palate and propelling a bolus to the hypopharyngeal space at the back of the mouth/top of the throat. During this process, there is a significant spatial/temporal pressure pattern. For example, the magnitude of pressure is highest near the front of the mouth and, during a swallow, negative pressure is generated resulting from suction of the bolus and tongue movement (see, e.g., Ono et al., *Dysphagia* 19:259-264, 2004; and Kennedy et al., *Dysphagia* 25:11-19, 2010). An array of sensors in a retainer (or other similar dental appliance on the hard palate) can sense these pressures to trigger swallowing. One example of such a device is shown in FIGS. 6-15. A device similar or identical to the one in FIG. 6 could be used to sense interoral pressure signals during swallowing and function as a control source for laryngeal elevation and/or vocal fold movement. As shown in FIG. 15 (indicated by thick black line), it will be appreciated that a program comprising a swallow recognition algorithm can be used along with the device to record pressure signals and generate output(s) a "trigger" signal on recognition of activity (e.g., swallowing, chewing, etc.);

(c) hypopharyngeal pressure sensor(s)—elevation of hypopharyngeal pressure is a key component of the initiation of a swallow. The pressure in the hypopharynx can be sensed with a pressure sensor (e.g., as part of a denture appliance) located at the back of the oral cavity (e.g., over the molar teeth):

(d) inner ear pressure sensor(s)—a surrogate to direct pressure sensing in the hypopharynx is the pressure change that occurs in the inner ear (i.e., transmitted through the Eustachian tubes) during a swallow. A sensor (e.g., formed as part of an ear plug) placed in or over the ear canal can sense this pressure change;

(e) nasalis EMG sensor(s)—during a swallow event, the airway passages are opened reflexively by the nasalis muscle. Detection of nasalis EMG activity can be used to control swallowing;

(f) superior laryngeal nerve (SLN) activity sensor(s)—the SLN largely includes sensory components from the laryngeal space and epiglottis. The presence of material in this space activates these sensory components. Recording SLN activity can be used to control swallowing by the presence of material in the laryngeal space;

(g) submandibular, lingual, and/or glossopharyngeal nerve activity sensor(s)—these nerves contain sensory fibers from the tongue and other elements along the food path, including taste buds, vallate papillae, and posterior tongue regions involved with swallow initiation. Detecting activity of one or more of these nerves can be used to modulate upper airway disorders; and (h) soft palate EMG sensor(s)—the tensor veli palatini and the levator veli palatini are responsible for moving the soft palate and thereby blocking the nasal passage during swallowing. EMG activity of the tensor veli palatini and/or levator veli palatini (as accessible via the nasal passage) can be used as a control source for laryngeal elevation and/or vocal fold movement according to one aspect of the present invention.

Advantageously, the method 10 of the present invention provides a hybrid approach for modulating upper airway function in a subject. Unlike prior art methods that separately control laryngeal motion and vocal fold movement, the present invention takes advantage of the discovery that each of these mechanisms contributes to proper upper airway function and is dependent upon the etiology and condition of the subject. Consequently, the present invention provides a hybrid approach to modulating upper airway function that combines muscle- or nerve-based stimulation of at least one extrinsic laryngeal muscle with muscle- or nerve-based stimulation of at least one intrinsic laryngeal muscle.

Figure 16:
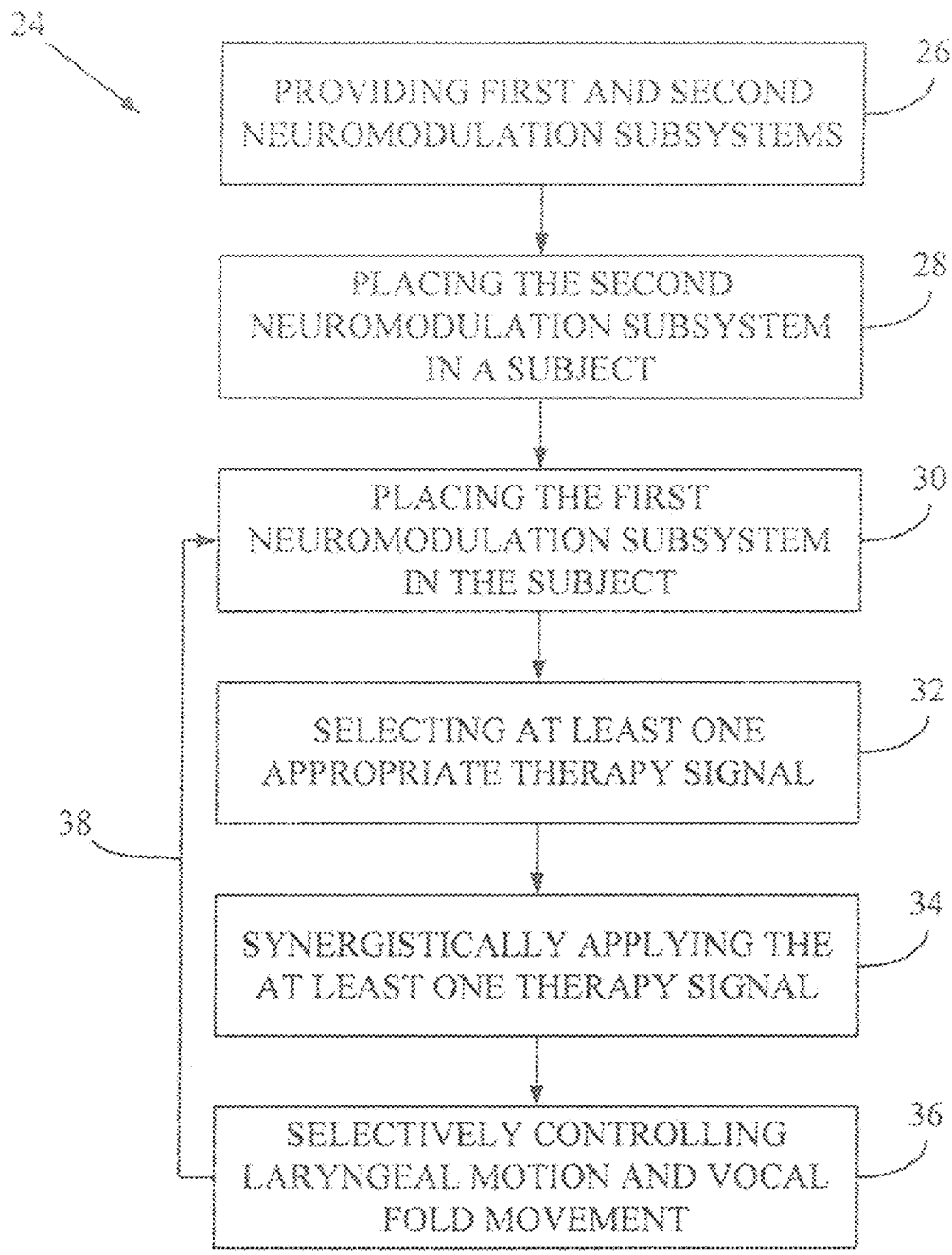
FIG. 16 is process flow diagram exemplifying the method shown in FIG. 5.

FIG. 16 illustrates one example of the present invention comprising a hybrid method 24 for modulating upper airway function in a subject. As shown in FIG. 16, one step of the method 24 can include providing a neuromodulation system at Step 26. The neuromodulation system can comprise a first neuromodulation subsystem, a second neuromodulation subsystem, and a controller in communication with the first and second neuromodulation subsystems. As described above, the controller can comprise a microprocessor, a hardwired circuit, or other appropriate means for controlling various components of the neuromodulation system.

One or both of the first and second neuromodulation subsystems can be configured as an open- or closed-loop system (as described above). In an open-loop system, for example, the first neuromodulation subsystem can comprise an electrode array, a first signal generator, and a first power source, all of which are in electrical communication with one another. Alternatively, in a closed-loop system, the first neuromodulation subsystem can comprise an electrode array, a sensor array, a first signal generator, and a first power source, all of which are in electrical communication with one another.

Figure 17:
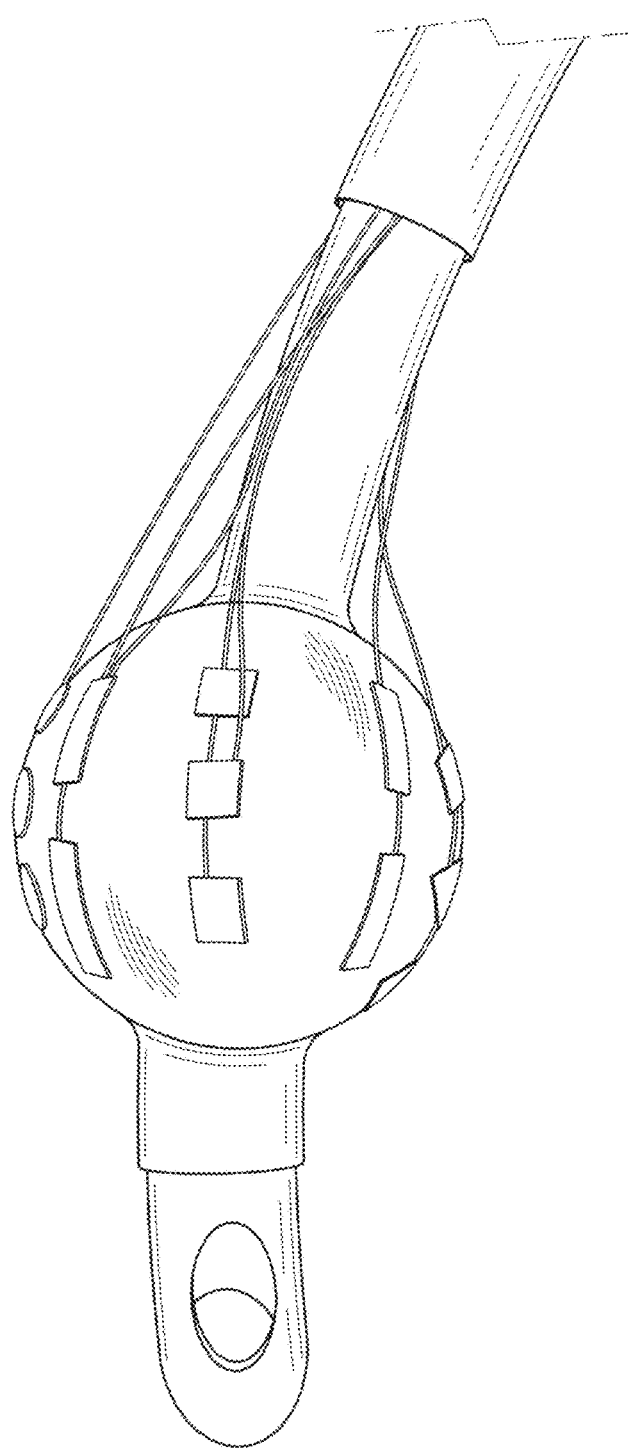
FIG. 17 is an image showing a trans-tracheal electrode support structure constructed in accordance with another aspect of the present invention.

The first neuromodulation subsystem can additionally include an electrode support structure capable of supporting at least one of the electrode array and the sensor array. The electrode support structure can comprise any flexible or semi-flexible structure adapted for acute, semi-chronic, or chronic placement in a portion of a subject's trachea. One example of an electrode support structure is shown in FIG. 17. For acute placement, for example, the electrode support structure can have a configuration similar to an endotracheal tube. Alternatively, for semi-chronic or chronic placement, the electrode support structure can have a segmented, tube-like configuration. The electrode array (and optionally the sensor array) can be securely disposed on or within the electrode support structure. Alternative configurations of the electrode support structure can include: a cuff-shaped device that includes at least one electrode and is capable of being placed about a standard endotracheal tube; an endotracheal tube with at least one electrode that is integrated therein; and a Peterson-type electrode that is capable of being securely disposed within one of the annular ligaments that extends between the cartilaginous rings of the trachea. The electrode support structure can be made of any one or combination of known biocompatible and electrically-insulative materials, such as silicone. The delivery route of the electrode support structure will depend upon the nature of the electrode support structure, the disease(s) being treated by the present invention, and/or the general medical condition of the subject. Examples of suitable delivery routes can include trans-oral and trans-nasal routes.

As noted above, the second neuromodulation subsystem can be configured as an open- or closed-loop system. In an open-loop system, for example, the second neuromodulation subsystem can comprise an electrode array, a second signal generator, and a second power source, all of which are in electrical communication with one another. Alternatively, in a closed-loop system, the second neuromodulation subsystem can comprise an electrode array, a sensor array, a second signal generator, and a second power source, all of which are in electrical communication with one another. Examples of sensor arrays, electrode arrays, signal generators, and power sources that may be used as part of the first and second neuromodulation subsystems are described above.

At Step 28, the second neuromodulation subsystem can be placed in the subject. The second neuromodulation subsystem can comprise, for example, an electrode array, a sensor array (e.g., at least one piezoelectric sensor), a second signal generator, at least one controller, and a second power source, all of which are in electrical communication with one another. Prior to placement, however, at least one extrinsic laryngeal muscle (e.g., anterior or posterior digastric muscles, geniohyoid muscle, stylohyoid muscle, thyrohyoid muscle, sternohyoid muscle) can be identified using visual confirmation, an imaging modality (e.g., MRI or CT), and/or selective neurostimulation techniques. Using neurostimulation, for example, an electrical current can be briefly delivered to at least one extrinsic laryngeal muscle to ensure proper placement of the electrode array.

Placement of the second neuromodulation subsystem can include disposing the controller, the second signal generator, and the second power source in a housing as a single unit. The housing can then be placed in a subcutaneous pocket (e.g., formed in the upper chest) of the subject. Alternatively, the controller, the second signal generator, and/or the second power source can be left external to the subject. One or more external devices, such as a hand switch can be optionally connected to the controller or otherwise placed in communication therewith for subject-controlled or open-loop upper airway modulation.

Next, the electrode and/or sensor arrays can be placed in either the same or different extrinsic laryngeal muscle(s). Both the electrode array and the sensor array can be in electrical communication with any of the components of the neuromodulation system, including an electrical lead or leads. The electrode and sensor arrays can be secured (e.g., using an adhesive, suture, bone anchor, or other means) at an exterior or interior location in or on the extrinsic laryngeal muscle(s). For example, the sensor array can be percutaneously placed by fixing the sensor array to a surface of the extrinsic laryngeal muscle or by inserting the sensor array into the extrinsic laryngeal muscle so that a physiological parameter of interest can be detected (e.g., pressure, acceleration, strain, force, etc.).

Figure 18A:
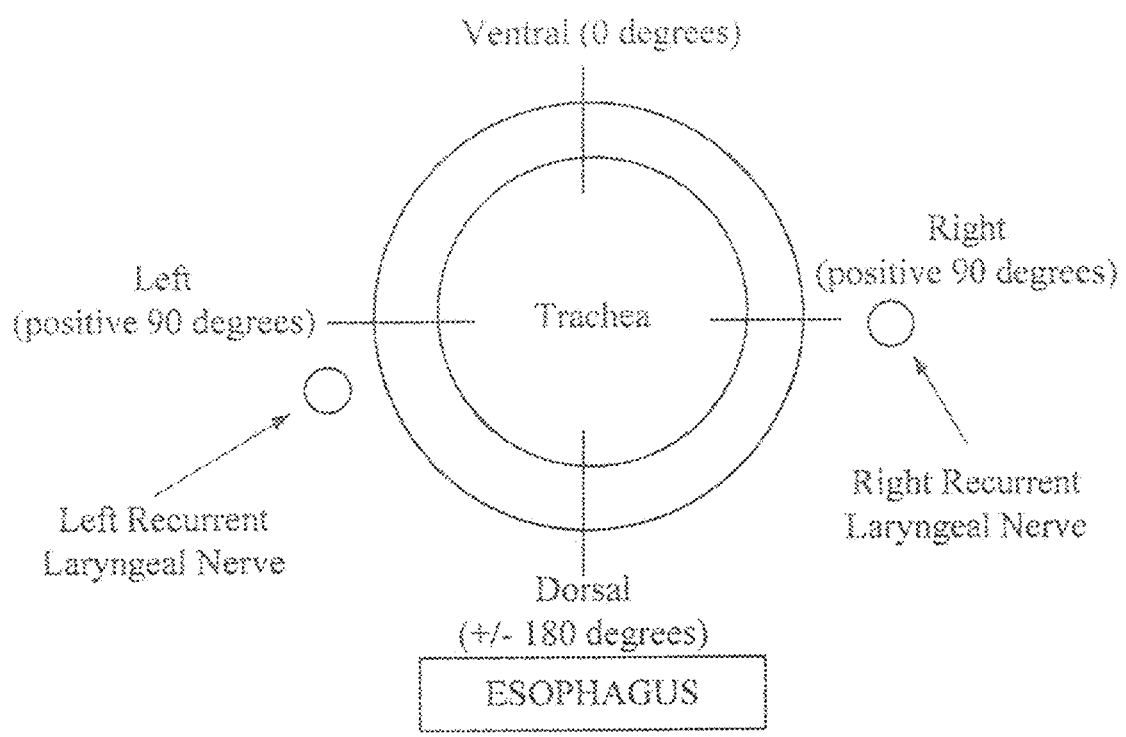
FIGS. 18A-B show the location of the recurrent laryngeal nerve (FIG. 18A) as determined by stimulation experiments (FIG. 18B)
Figure 18B:
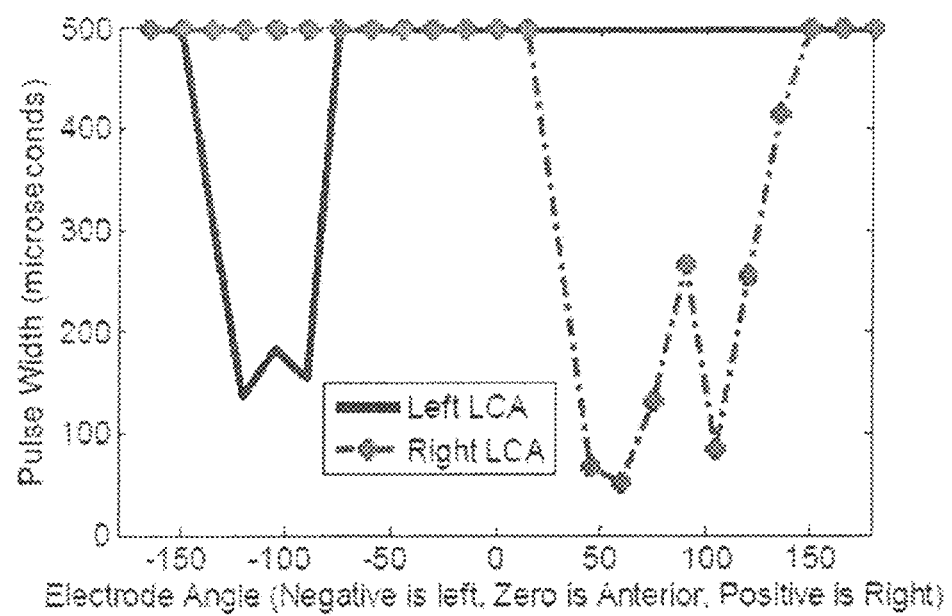

Following placement of the second neuromodulation subsystem, at least a portion of the first neuromodulation subsystem can be placed in the trachea of the subject (Step 30). Prior to placement, however, the RLN (e.g., the left RLN) can be identified using visual confirmation, an imaging modality (e.g., MRI or CT), and/or selective neurostimulation techniques. Using neurostimulation, for example, an electrical current can be briefly delivered to the RLN to ensure proper placement of the electrode support structure and, in particular, the electrode array. Advantageously, one aspect of the present invention provides for electrode placement in or about the trachea of a subject to ensure optimal stimulation of the left and right RLN. As shown in FIGS. 18A-B, for example, placement of a first electrode at about −150 degrees (e.g., about −120 degrees) to about −45 degrees (e.g., about −80 degrees) may be optimal for stimulation of the left RLN, while placement of a second electrode at about 60 degrees to about 165 degrees (e.g., about 100 degrees) may be optimal for right RLN stimulation. It will be appreciated that Step 30 of the method 24 can be performed either prior to or contemporaneous with Step 28.

As noted above, the configuration of the first neuromodulation subsystem can depend upon the intended application of the method 24. To modulate an upper airway of a subject for a semi-chronic period of time, for example, the first neuromodulation subsystem can comprise an electrode array, a sensor array, a first signal generator, and a first power source, all of which are in electrical communication with one another. Additionally, the first neuromodulation subsystem can comprise a flexible, tube-shaped electrode support structure having the electrode array operably connected thereto.

Placement of the first neuromodulation subsystem can begin by sedating the subject (either completely or partially) and then inserting the electrode support structure into the subject's trachea. Based on the previously determined location of the RLN, the electrode support structure can be situated in the subject's trachea so that at least a portion of the electrode array is in electrical communication with a portion of the RLN. Confirmation of proper electrode support structure placement can be made either during or after placement by briefly delivering electrical stimulation to the electrode array and verifying (e.g., visually) movement of the vocal folds. Depending upon the particular construction of the electrode support structure, all or only a portion of the electrode support structure can be securely placed in the trachea by embedding into the mucosa or press-fitting.

Depending upon the intended application of the method 24, the sensor array can be operably connected to the electrode support structure or, alternatively, positioned at a bodily location remote from the electrode support structure. For example, the sensor array can be integrated into a retainer (or other dental appliance) on the hard palate. Such a sensor array may be able to sense changes in pressures (i.e., during swallowing) and then communicate the sensed changes to other components of the first neuromodulation subsystem. It will be appreciated that other components of the first neuromodulation subsystem, such as the first power source and the first signal generator may be included as part of the retainer.

Following placement of the first and second neuromodulation subsystems, at least one appropriate therapy signal is selected at Step 32. The therapy signal can comprise one or more electrical signals capable of modulating the RLN and/or at least one extrinsic laryngeal muscle of a subject. The therapy signal can have a desired strength and timing that is based on a variety of considerations, such as the location of the first and second neuromodulation subsystems, the overall health of the subject (e.g., external or internal), the particular upper airway disorder from which the subject is suffering, the severity of the upper airway disorder, any co-existing morbidities, and/or current medication dosage by the subject. In a subject suffering from aspiration, for example, first and second therapy signals can be selected so that synergistic control of vocal fold movement and laryngeal motion is possible. To modulate vocal fold movement, for example, a therapy signal having a relatively low frequency can be applied to the RLN to promote vocal fold opening, while a therapy signal having a relatively high frequency can be applied to the RLN to promote vocal fold closing.

At Step 34, at least one appropriate therapy signal (or signals) can be applied to the RLN and at least one extrinsic laryngeal muscle to synergistically control laryngeal motion and vocal fold movement. As described above, the therapy signal can be delivered to one or more of the electrodes comprising the electrode array of each of the first and second neuromodulation subsystems either continuously, periodically, episodically, and/or a combination thereof. The therapy signal can be delivered to one or both of the electrode arrays all at once or, alternatively, to only a select number of electrodes comprising the electrode arrays. The particular voltage, current, and frequency of the therapy signal may be varied as needed.

At Step 36, the first and second neuromodulation subsystems can be activated to selectively control vocal fold movement and laryngeal motion, respectively. The stimulation parameters of the therapy signal(s) (e.g., frequency, voltage, etc.) can be varied as needed so that intrinsic laryngeal muscle function (via RLN stimulation) and extrinsic laryngeal muscle function are synergistically controlled. This, in turn, can cause each mechanism to contribute to improving upper airway function. For example, the stimulation parameters of a first therapy signal can be optimized to promote vocal fold closure, while the stimulation parameters of a second therapy signal can be optimized to promote laryngeal motion (e.g., elevation) of the hyolaryngeal complex (e.g., by directly stimulating a single one of the hyoglossus, the posterior belly of the digastric, or the stylohyoid muscles).

It will be appreciated that the method 24 can alternatively omit the second neuromodulation subsystem so that only the first neuromodulation subsystem is used to treat an upper airway disorder in a subject. For example, a first neuromodulation subsystem having a closed-loop configuration can be placed in the trachea of a subject suffering from aspiration or laryngospasm. As described above, the electrode support structure can be inserted into the subject's trachea and, based on the previously determined location of the RLN, positioned so that at least a portion of the electrode array is in electrical communication with a portion of the RLN. Next, the sensor array can be operably connected to the electrode support structure or, alternatively, positioned at a bodily location remote from the electrode support structure. If it has not been done so already, the remaining components of the first neuromodulation subsystem can then be placed in or on the subject. Following placement of the first neuromodulation subsystem, at least one appropriate therapy signal capable of modulating the RLN can be delivered to the electrode array. The therapy signal can be delivered to the electrode array to selectively affect vocal fold movement and prevent or mitigate aspiration or laryngospasm in the subject.

Another aspect of the present invention includes a method 40 (FIG. 19) for treating laryngospasm in a subject. Laryngospasm is an uncontrolled/involuntary muscular contraction of the vocal folds. The condition typically lasts between about 30 and 60 seconds, and at least partially obstructs the subject's ability to inspire and breathe normally. Laryngospasm may be triggered when the vocal folds or the area of the trachea below the vocal folds detects the entry of water, mucus, blood, or other substance. Laryngospasm is characterized by stridor and/or retractions, and some people suffer from frequent laryngospasms whether awake or asleep.

One of the present concerns with RLN stimulation is possible laryngospasm associated with positive sensory feedback loops. As a result of this concern, RLN stimulation prior art has required inclusion of a tracheostomy. The present invention, however, provides a method 40 for treating laryngospasm by use of high-frequency or blocking stimulation of the RLN. Since the nerve fibers that innervate the intrinsic laryngeal closing muscles comprise the RLN, blocking nerve conduction through substantially all of the axons in the RLN can mitigate or stop muscle spasm and thereby allow a subject to breathe until the reflexive episode has passed, without the need for tracheostomy.

Figure 19:
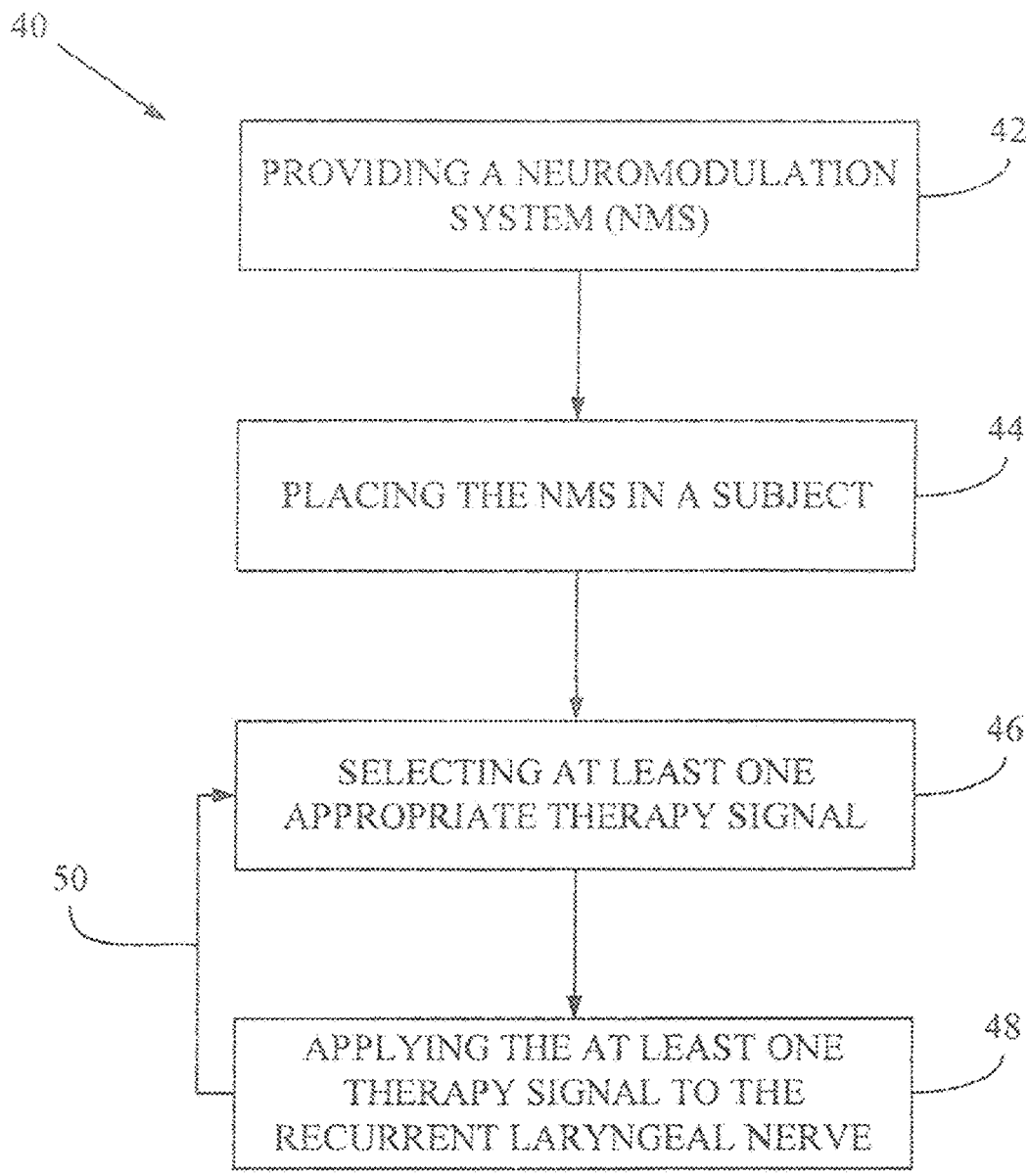
FIG. 19 is a process flow diagram illustrating a method for treating laryngospasm in a subject according to another aspect of the present invention.

As shown in FIG. 19, the method 40 includes providing a neuromodulation system at Step 42. The neuromodulation system can be configured in an identical or similar manner as the neuromodulation system described above. For example, the neuromodulation system can comprise a controller, a signal generator, an electrode array, a sensor array, and a power source. As discussed above, the various components of the neuromodulation system can communicate with one another via a variety of mechanisms, such as direct electrical communication, RF communication, magnetic communication, optical communication, sonic communication, and combinations thereof.

At Step 44, all or only a portion of the neuromodulation system is placed in the subject. Prior to placement, however, the RLN can be identified using, for example, visual confirmation, an imaging modality (e.g., MRI or CT), and/or selective neurostimulation. Using neurostimulation, for example, an electrical current can be briefly delivered to the RLN to ensure proper electrode location.

As discussed above, placement of the neuromodulation system can include disposing the controller, the signal generator, and the power source in a housing as a single unit. Additionally, placement of the neuromodulation system can include placing at least one electrode, such as a FINE electrode into electrical communication with the RLN. Alternatively, the controller, signal generator, and/or power source can be left external to the subject where, for example, the electrode array includes self-contained electrodes. One or more external devices can be optionally connected to the controller or otherwise placed in communication therewith for subject-controlled (i.e., open-loop) vocal fold modulation.

Alternatively, and as discussed above, placement of the neuromodulation system can include intra-tracheal placement of an electrode support structure. The electrode support structure can be placed in the trachea to ensure optimal stimulation of the left and right RLN. As noted above, placement of a first electrode at about −150 degrees (e.g., about −120 degrees) to about −45 degrees (e.g., about −80 degrees) may be optimal for stimulation of the left RLN, while placement of a second electrode at about 60 degrees to about 165 degrees (e.g., about 100 degrees) may be optimal for right RLN stimulation.

At Step 46, at least one appropriate therapy signal is selected for application to the RLN. The RLN is a branch of the vagus nerve and supplies motor function and sensation to the larynx. In particular, the intrinsic laryngeal muscles that control vocal fold movement are innervated by the RLN. Given these physiological considerations, an appropriate therapy signal is selected so that application of the therapy signal to the RLN can block or mitigate nerve conduction through substantially all of the RLN axons that innervate the intrinsic laryngeal muscles. Thus, the therapy signal can comprise one or more periodic or continuous electrical signals capable of blocking or mitigating nerve conduction through substantially all of the RLN axons.

After selecting the appropriate therapy signal, the therapy signal is applied to the RLN at Step 48. In particular, the therapy signal is applied to the RLN at the onset or during the occurrence of laryngospasm in the subject. The therapy signal can be applied to the RLN at a strength and frequency sufficient to mitigate or stop spasm of the intrinsic laryngeal muscles. This, in turn, permits vocal fold opening during the spasm and allows the subject to breathe until the reflexive episode has passed.

The therapy signal can be applied to the RLN as part of either an open- or closed-loop system (Step 50). In an open-loop system, for example, a medical professional or the subject may, at any time, manually or by the use of a device adjust therapy signal parameters (e.g., pulse-amplitude, pulse-width, pulse-frequency, or duty cycle). For example, an open-loop system can be initiated in response to a subject prompt (i.e., during laryngospasm) via an external switch or sensor, such as a hand switch or via voice command, motion sensor, or one or more of the sensors of the sensor array.

In a closed-loop system, the strength and timing of the therapy signal(s) can be altered in response to a physiological parameter of interest, such as force, movement, pressure, position, displacement, myoelectrical activity, and/or nerve conduction or neuroelectrical activity. For example, the neuromodulation system can include at least one sensor capable of detecting vocal fold movement. If, during delivery of the therapy signal to the electrode array, the vocal folds do not sufficiently open to permit the subject to breathe during laryngospasm, the sensor can communicate with the neuromodulation system to vary the strength and/or frequency of the therapy signal and ensure that the vocal folds remain sufficiently open during the reflexive episode.

Advantageously, the method 40 of the present invention removes the need for tracheostomy in subjects experiencing laryngospasm while also reducing or eliminating the risk of oxygen starvation during reflexive episodes. By providing blocking stimulation to the RLN at the onset or during the occurrence of laryngospasm and thereby preventing or mitigating nerve conduction through the RLN axons, the method 40 permits a subject to breathe until the laryngospasm has passed.

The following examples are for the purpose of illustration only and are not intended to limit the scope of the claims, which are appended hereto.

EXAMPLE 1

The following study demonstrates targeted transtracheal stimulation for laryngeal muscle activation.

Nine healthy canines were used in this study. Average mass was 15.6 kg (range 14.2-17.5 kg). The canines were anesthetized with an initial intravenous dose of sodium thiopental and were maintained under anesthesia with vaporized isofluorine provided via endotracheal tube. The canine was laid in a supine position.

A midline incision was cut along the ventral neck and the trachea and larynx were exposed. Pairs of 0.004" diameter hooked wire electrodes were implanted bilaterally into the Posterior Cricoarytenoids, Lateral Cricoarytenoids, Thyroarytenoids, and Cricothyroids using a 22-gauge needle. A tracheotomy was performed below the third tracheal cartilage and a modified endotracheal tube (FIG. 17) with surface electrodes attached to the tracheal tube's inflatable cuff was inserted. The locations of the electrodes on the tracheal cuff were recorded and marked up the length of the tube to obtain the exact angular location of each electrode. Pairs of electrodes were spaced at regular intervals of 45 degrees around the perimeter of the tracheal cuff to enable bipolar stimulation parallel to the direction of the trachea. The leads to the electrodes passed through the tracheotomy for stimulation.

Stimulation was provided by a custom-built stimulator (Crishtronics, Cleveland, Ohio) controlled by laptop computer and a custom Matlab program. Electromyography recordings from the eight implanted muscles were processed through CED amplifiers (Cambridge Electronic Designs, Cambridge, England) with a bandpass filter from 10 Hz to 2000 Hz. Data was collected using a BNC-2110 DAQ (National Instruments, Austin, Tex.) at a sampling frequency of 2400 Hz per channel. Stimulation pulse trains (0-5 mA, 0-500 microsecond, 4 Hz) were used to generate recruitment curves of each muscle's activation for each electrode location tested (every 15 degrees for 360 degrees).

Videos of vocal fold movement were made using a laryngoscope (JEDMED ENT-3L, St. Louis, Mo.) and recorded to a Panasonic DVR (DMR-EH55) at 30 frames per second. The laryngoscope was positioned and stabilized so that the camera would not move during recording. For laryngoscopic recording, transtracheal stimulation (0-5 mA, 100-500 microsecond, 5-50 Hz) was performed to view vocal fold adduction. Stimulation was applied to either the left, right or both sides of the trachea to obtain comparisons of the electrodes' effects. Each stimulation train was applied for at least 5 seconds followed by a period of no stimulation for 5 seconds.

Videos of vocal fold movement were recorded and digitally analyzed for pixel count of glottal opening area in Matlab. The glottal area was selected and threshold contrasting was used to separate the lighter vocal folds from the darker glottal area. The number of pixels detected as glottal area was recorded for each frame and plotted over time.

Figure 20:
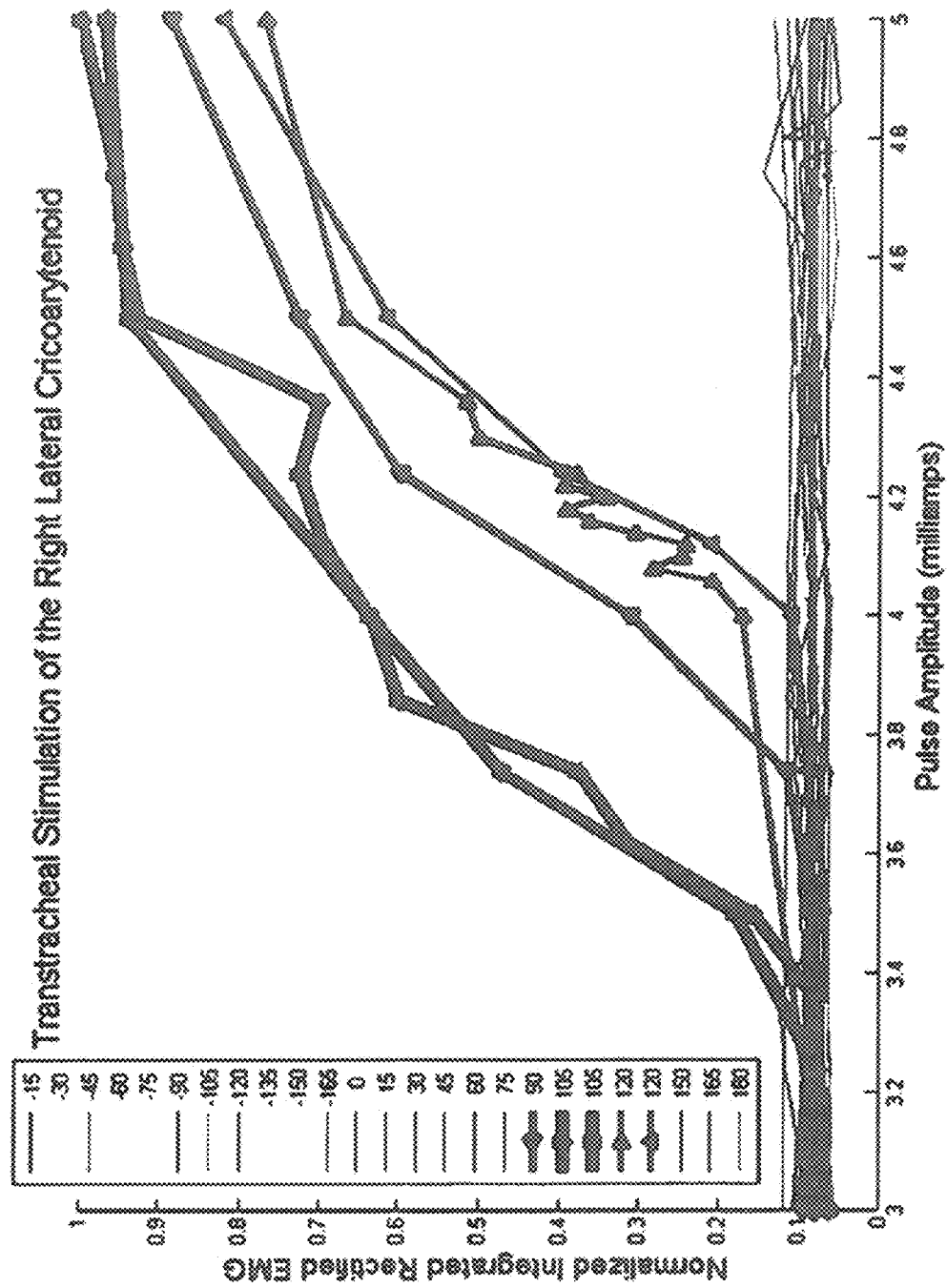
FIG. 20 is a plot showing recruitment curves for the right lateral cricoarytenoid caused by transtracheal stimulation at several points around the tracheal wall.

For each electrode location, a series of 4 Hz pulses was applied and the resulting EMG activation was recorded. A single pulse width was set and the pulse amplitude was varied. The resulting EMG twitch activation was rectified, integrated, and normalized to the maximum twitch EMG for that muscle recorded during the entire experiment. In a low noise situation, the normalized, integrated, rectified EMG should be less than 0.1 when the stimulation threshold is not reached and near to 1 when a sufficient stimulation pulse is provided. While most electrodes (−165 through 75, 150-180 degrees) have no activation over 0.15, when the electrodes located at angles between 90 and 120 degrees the normalized activation increased (FIG. 20). For electrodes at 105 degrees right, at a stimulus level of 3.8 mA the Right lateral Cricoarytenoid reached 50% of its maximum activation, while none of the other location have increased above 20%. To obtain 50% activation at 90 degrees, 4.2 mA was required, and to obtain 50% activation at 120 degrees, 4.3 mA were required. At all other locations, greater than 5 mA was required.

Figure 21:
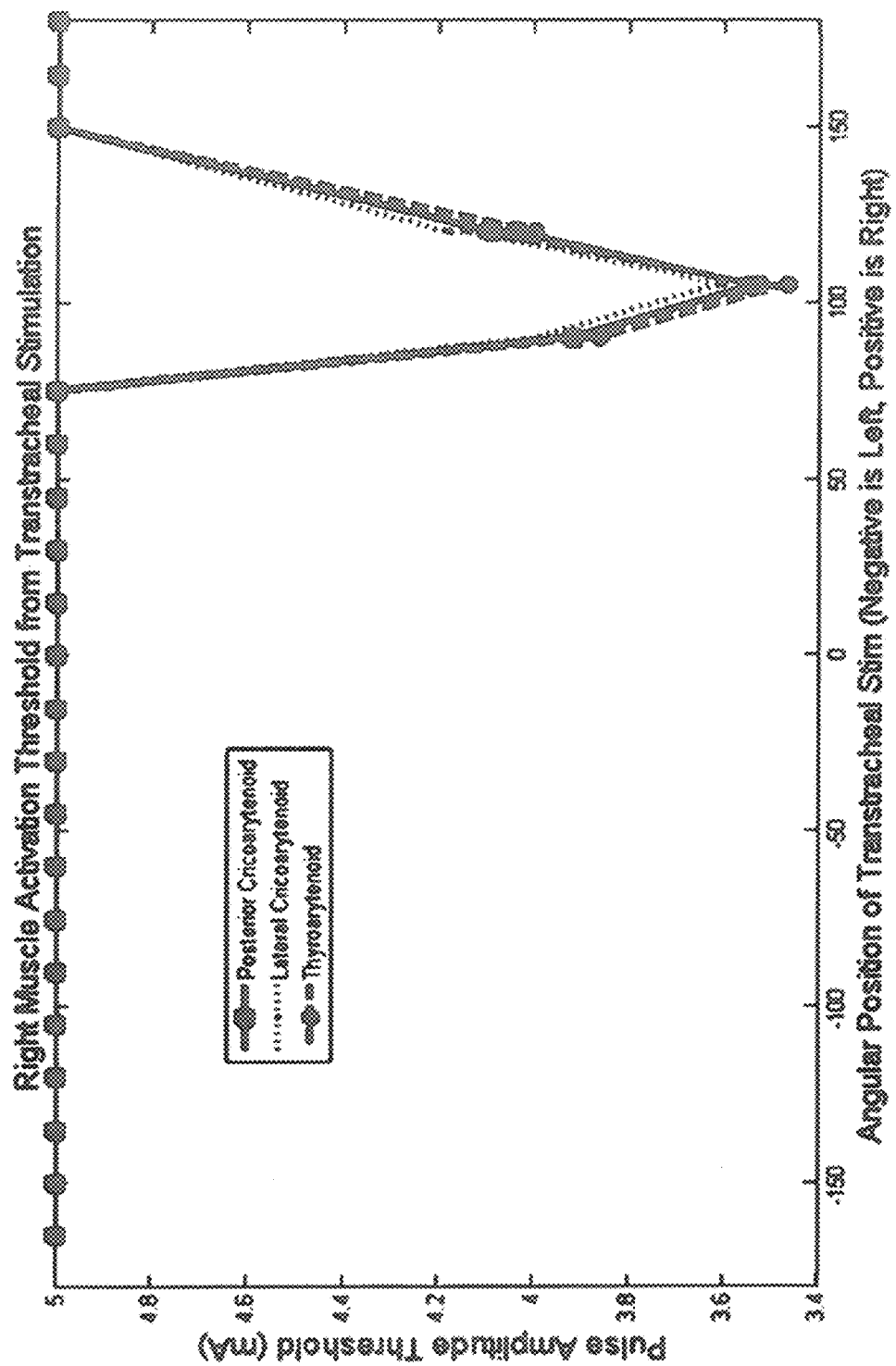
FIG. 21 is a plot showing threshold as a function of electrode location around the tracheal wall (0° is defined as the ventral center of the trachea, and angles between 0° and 180° are to the right and between 0° and −180° are to the left)

The 105 degree right location has the lowest pulse amplitude threshold, defined as 20% activation of the muscle, for the three muscles of the right larynx that are enervated by the recurrent laryngeal nerve (FIG. 21). Threshold was defined as 20% of muscular activation. All three right muscles exhibit the same pattern of activation in relation to contact location.

The optimal location for stimulation on the right side of the trachea is 105 degrees in two subjects, 135 in three subjects, 150 degrees in one subject, and 165 degrees in two subjects. All but one of the subjects had an activation threshold below 5 mA at 135 degrees right.

On the left side, the minimum activation threshold was found at 45 degrees for one subject, 60 degrees for one subject, 90 degrees for two subjects, 120 degrees for two subjects and 150 degrees for one subject. No single site had an activation threshold of less than 5 mA for more than 4 subjects.

Figure 22:
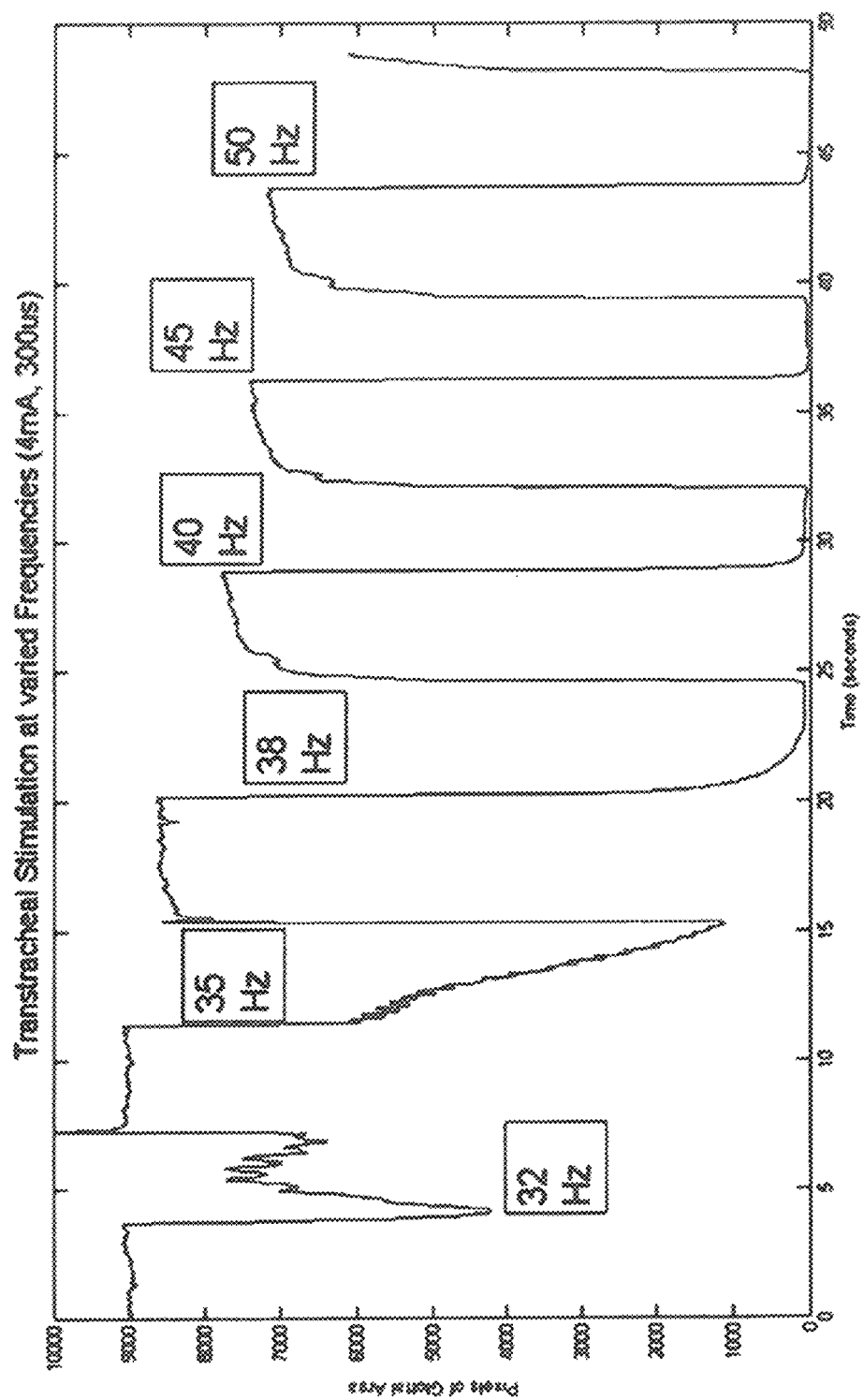
FIG. 22 is a plot showing the area of glottal opening (the area is represented in arbitrary units, with 0 corresponding to complete closure)

The glottal area was plotted over time (FIG. 22). The onset of stimulation causes a sharp decrease in the area of the glottal opening. For frequencies greater than 40 Hz, the average reduction in vocal fold area is 82.8% among all transtracheal stimulations (standard deviation 22.2 percent, n=9). Variations in position of the electrodes cause significant variation in the capabilities of the electrodes, ranging from certain locations causing no change to some causing an average of 99.8% (standard deviation 0.3%, n=3).

In conclusion, transtracheal stimulation is capable of causing complete vocal fold closure and maintaining that closure via optimal intatracheal electrode placement.

EXAMPLE 2

Four healthy canines were used in this study. Average mass was 15.9 kg (range 14.2-17.5 kg). The canines were anesthetized with an initial intravenous dose of sodium thiopental and were maintained under anesthesia with vaporized isofluorine provided via endotracheal tube. The canines were laid in a supine position.

In three of the canines, incisions were made approximately 3 cm lateral of the midline on the ventral neck at the location of the hyoid cartilage. In the other canine, a midline incision was cut along the ventral neck over the hyoid. From these incisions, the hypoglossal nerve was bilaterally exposed and three nerve cuffs were placed onto branches of the nerve. One cuff went onto the branch off of the hypoglossal enervating the thyrohyoid. A second cuff went onto the branch off of the hypoglossal continuing to the geniohyoid and genioglossal muscles. The third cuff went onto the original trunk of the hypoglossal, which contains both branches.

Pairs of 0.004" diameter hooked wire electrodes were implanted bilaterally into the Geniohyoids, Mylohyoids, Thyrohyoids, and Genioglossi muscles using a 22-gauge needle. The tip of the hooked wire electrode was bared of insulation for 1-3 mm. The leads were passed through the incision and the incision was sutured.

Colored markers were placed onto metal clips which were then sutured to the thyroid and hyoid cartilages along a midline incision. A third colored marker was adhered to either the surface of the skin or a stationary location on the table.

Stimulation was provided using a custom-made stimulator (Crishtronics, Cleveland, Ohio) controlled by laptop computer and a custom Matlab program or by AFG 3022Bwaveform generator (Tektronix, Beaverton, Oreg.). Electromyography recordings from the eight implanted muscles were processed through CED amplifiers (Cambridge Electronic Designs, Cambridge, England) with a bandpass filter from 10 Hz to 2000 Hz. Data was collected using a BNC-2110 DAQ (National Instruments, Austin, Tex.) at a sampling frequency of 2400 Hz per channel. Stimulation pulse trains (0-5 mA, 0-500 microsecond, 4 Hz) were used to generate recruitment curves of each muscle's activation for each electrode location tested (six cuffs, 2-10 contacts per electrode).

A video camcorder (Panasonic 3CCD Mini DV) was placed level with the canine to view the three markers and their movement was recorded to a Panasonic DVR (DMR-EH55). Stimulation was provided (0-5 mA, 100-500 microseconds, 5-40 Hz) to contacts on each of the nerve cuffs. Each bilateral pair of cuffs would be stimulated individually then together, each for five seconds to allow tetany to be reached. Additionally, the hooked wire electrodes were directly stimulated while video was recorded.

Videos of movement were digitally analyzed offline using Matlab. The distance between markers was recorded. Distances between markers and the stable edge of the video frame were then exported for analysis to measure the effect of each muscle and the velocity of elevation motion.

Figure 23:
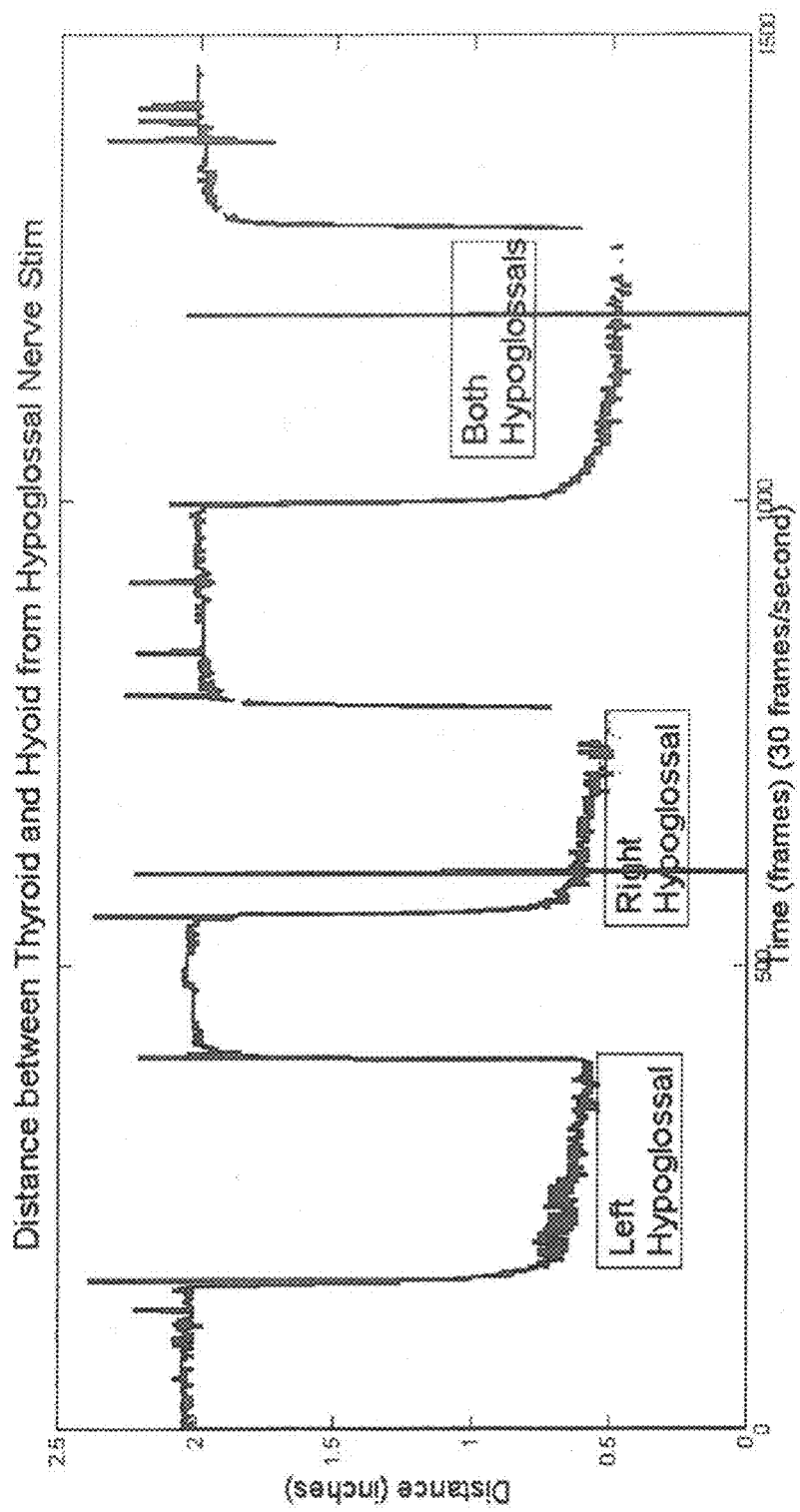
FIG. 23 is a plot showing separation of the thyroid and hyoid. During stimulation, the thyroid cartilage and hyoid bone are brought closer together, while the hyoid bone is also moved closer to the arch of the mandible (not shown).

The distance between the thyroid and hyoid markers when stimulation is applied rapidly decreases, followed by a slow continued contraction as tetany is achieved (FIG. 23). This can be seen for stimulation of each individual cuff (left and right) as well as the simultaneous stimulation of both cuffs.

Stimulation of the nerve cuff contacts on the hypoglossal nerves caused an average of 1.58 centimeters of hyoid elevation (standard deviation 0.16 cm, n=6). Those same contacts caused an average contraction of Thyroid-Hyoid distance of 0.71 cm (standard deviation 0.21 cm, n=6). Direct muscle stimulation caused an average contraction of the Thyroid-Hyoid distance of 0.59 cm (standard deviation 0.05 cm, n=3).

Both nerve cuff stimulation and intramuscular stimulation cause the laryngeal elevation that is desired to replicate the swallowing motion. The elevation occurs rapidly then stabilizes at a plateau of maximum contraction, enabling the maintenance of superior-anterior movement for airway protection.

From the above description of the invention, those skilled in the art will perceive improvements, changes and modifications. Such improvements, changes, and modifications are within the skill of the art and are intended to be covered by the appended claims.

Having described the invention, the following is claimed:

1. A method, comprising the steps of:
    delivering a first therapy signal to modulate an extrinsic laryngeal muscle of a subject according to a first timing parameter to promote anteriosuperior motion of the hyolaryngeal complex;
    delivering a second therapy signal to modulate a recurrent laryngeal nerve (RLN) of the subject according to a second timing parameter to promote vocal fold closure; and
    adjusting, by a controller comprising a processor, the first timing parameter of the first therapy signal and the second timing parameter of the second therapy signal, based on an input related to at least one sensed physiological signal or a volitional signal, to promote swallowing based on synergistic anteriosuperior motion of the hyolaryngeal complex and the vocal fold closure to prevent or mitigate aspiration in the subject during a swallow cycle.

2. The method of claim 1, wherein the first therapy signal is delivered by a first electrode, and
    wherein the second therapy signal is delivered by a second electrode.

3. The method of claim 1, further comprising adjusting a strength parameter of the first therapy signal or the second therapy signal based on a sensed parameter of interest.

4. The method of claim 3, wherein the sensed parameter of interest changes based on a volitional input.

5. The method of claim 1, wherein the first timing parameter and the second timing parameter are adjusted to treat an upper airway disorder.

6. The method of claim 5, wherein the upper airway disorder is at least one of a swallow cycle disorder of the subject, a laryngeal disorder of the subject, and a laryngospasm of the subject.

7. The method of claim 1, further comprising:
    sensing a change in a physiological parameter of interest; and
    adjusting a strength parameter of the first therapy signal or the second therapy signal based on the sensed change in the physiological parameter of interest.

8. A controller device comprising:
    a memory storing computer-executable instructions; and
    a processor to execute the computer-executable instructions to at least:
        set a first timing parameter of a first therapy signal, wherein the first therapy signal is delivered to a nerve innervating an extrinsic laryngeal muscle of a subject to promote anteriosuperior motion of a hyolaryngeal complex;
        set a second timing parameter of a second therapy signal, wherein the second therapy signal is delivered to a recurrent laryngeal nerve (RLN) of the subject to promote vocal fold closure;
        receive an input related to at least one of a physiological parameter detected by a sensor and a volitional input; and
        adjust the first timing parameter of the first therapy signal and the second timing parameter of the second therapy signal to promote swallowing based on synergistic anteriosuperior motion of the hyolaryngeal complex and the vocal fold closure to prevent or mitigate aspiration in the subject during a swallow cycle based on the input.

9. The controller of claim 8, wherein the processor further executes the computer-executable instructions to adjust a strength parameter of the first therapy signal or the second therapy signal based on a change in a sensed physiological parameter.

10. The controller of claim 8, wherein the controller is configured to be coupled to at least one sensor to sense the change in the physiological parameter.

11. The controller of claim 10, wherein the sensor is selected from the group consisting of a submental EMG sensor, a palatal tongue pressure sensor, a hypopharyngeal pressure sensor, an inner ear pressure sensor, a nasalis EMG sensor, a superior laryngeal nerve activity sensor, a submandibular nerve activity sensor, a lingual nerve activity sensor, a glossopharyngeal nerve activity sensor, and a soft palate EMG sensor.

12. The controller of claim 8, wherein the first timing parameter of the first therapy signal and the second timing parameter of the second therapy signal are adjusted to treat an upper airway disorder.

13. The controller of claim 12, wherein the upper airway disorder is at least one of a swallow cycle disorder of the subject, a laryngeal disorder of the subject, and a laryngospasm of the subject.

* * * * *